(12) United States Patent
Galbo et al.

(10) Patent No.: US 6,409,941 B1
(45) Date of Patent: *Jun. 25, 2002

(54) BLOCK OLIGOMERS CONTAINING 1-HYDROCARBYLOXY-2,2,6,6-TETRAMETHYL-4-PIPERIDYL GROUPS AS STABILIZERS FOR ORGANIC MATERIALS

(75) Inventors: James Peter Galbo, Wingdale, NY (US); Nicola Lelli, Basel (CH); Valerio Borzatta, Bologna (IT); Jean-Pierre Wolf, Courtaman (CH); Michael Ackerman, New City, NY (US); Piero Piccinelli, Sasso Marconi (IT)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/424,141
(22) PCT Filed: May 14, 1998
(86) PCT No.: PCT/IB98/00715
§ 371 (c)(1),
(2), (4) Date: Nov. 18, 1999
(87) PCT Pub. No.: WO98/54175
PCT Pub. Date: Dec. 3, 1998

(30) Foreign Application Priority Data

May 27, 1997 (EP) .............................. 97810328

(51) Int. Cl.$^7$ ................... C07D 401/12; C07D 401/14; C08K 5/3492
(52) U.S. Cl. ................ 252/401; 252/403; 524/97; 524/100; 544/198; 544/209; 544/215
(58) Field of Search ................. 544/198, 209, 544/219; 524/100, 97; 252/401, 403

(56) References Cited

U.S. PATENT DOCUMENTS

| | | | |
|---|---|---|---|
| 4,086,204 A | 4/1978 | Cassandrini et al. | 260/45.8 |
| 4,234,707 A | 11/1980 | Rody et al. | 525/437 |
| 4,331,586 A | 5/1982 | Hardy | 525/186 |
| 4,335,242 A | 6/1982 | Wiezer et al. | 544/198 |
| 4,459,395 A | 7/1984 | Cantatore | 524/100 |
| 4,492,791 A | 1/1985 | Orban et al. | 544/198 |
| 5,004,770 A | 4/1991 | Cortolano et al. | 524/99 |
| 5,096,950 A | 3/1992 | Galbo et al. | 524/99 |
| 5,124,378 A | 6/1992 | Behrens et al. | 524/95 |
| 5,204,473 A | 4/1993 | Winter et al. | 546/188 |
| 6,046,304 A * | 4/2000 | Borzatta et al. | 544/191 |
| 6,111,016 A * | 9/2000 | Katayama et al. | 525/88 |
| 6,114,420 A * | 9/2000 | Zedda et al. | 544/198 |
| 6,177,491 B1 * | 1/2001 | Galbo et al. | 544/198 |

FOREIGN PATENT DOCUMENTS

| | | |
|---|---|---|
| EP | 0053775 | 6/1982 |
| EP | 0309402 | 3/1989 |
| EP | 0357223 | 3/1990 |
| EP | 0377324 | 7/1990 |
| EP | 0389428 | 9/1990 |
| EP | 0435828 | 7/1991 |
| EP | 0462069 | 12/1991 |
| EP | 0782994 | 7/1997 |
| GB | 2301106 | 11/1996 |

OTHER PUBLICATIONS

Derwent Abstract 50507 E/25 for EP 53775 and Chem. Abstr. 97:183468d for EP 53775.

* cited by examiner

Primary Examiner—Richard L. Raymond
Assistant Examiner—Venkataraman Balasubrasubramanian
(74) Attorney, Agent, or Firm—David R. Crichton

(57) ABSTRACT

A product obtainable by transferring groups of formula (G-I) being present in a block oligomer having a polydispersity Mw/Mn of 1 to 1.7 and corresponding to formula (I) to groups of formula (Gu-II), wherein $R_1$ is a hydrocarbyl radical or —O—$R_1$ is oxyl; said transfer is carried out by reaction of the block oligomer with a hydroperoxide in a hydrocarbon solvent in the presence of a peroxide decomposing catalyst; n is a number from 2 to 14; $R_2$ is for example $C_2$–$C_{12}$alkylene; A is for example —N($R_4$)($R_5$); $R_4$ and $R_5$ are for example $C_1$–$C_{18}$alkyl; R is preferably a group of formula (G-I) and B and B* have one of the meanings given for A; with the proviso that in the individual recurrent units of formula (I), each of the radicals B, R and $R_2$ has the same or a different meaning. The products are useful as light stabilizers, heat stabilizers and oxidation stabilizers for organic materials, in particular synthetic polymers.

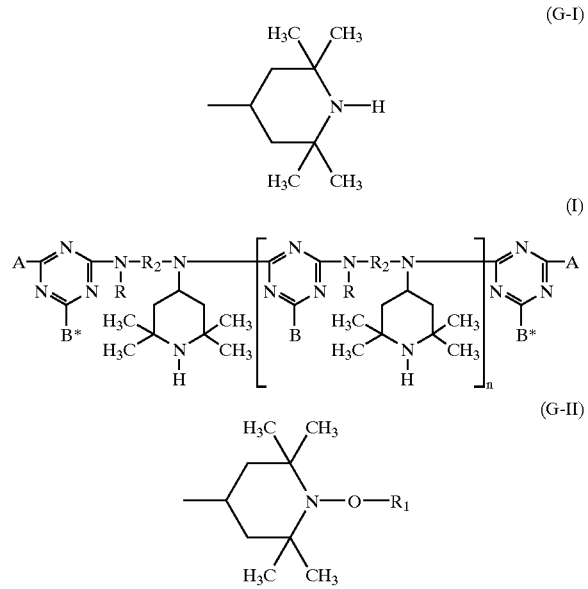

26 Claims, 2 Drawing Sheets

Figure 1:
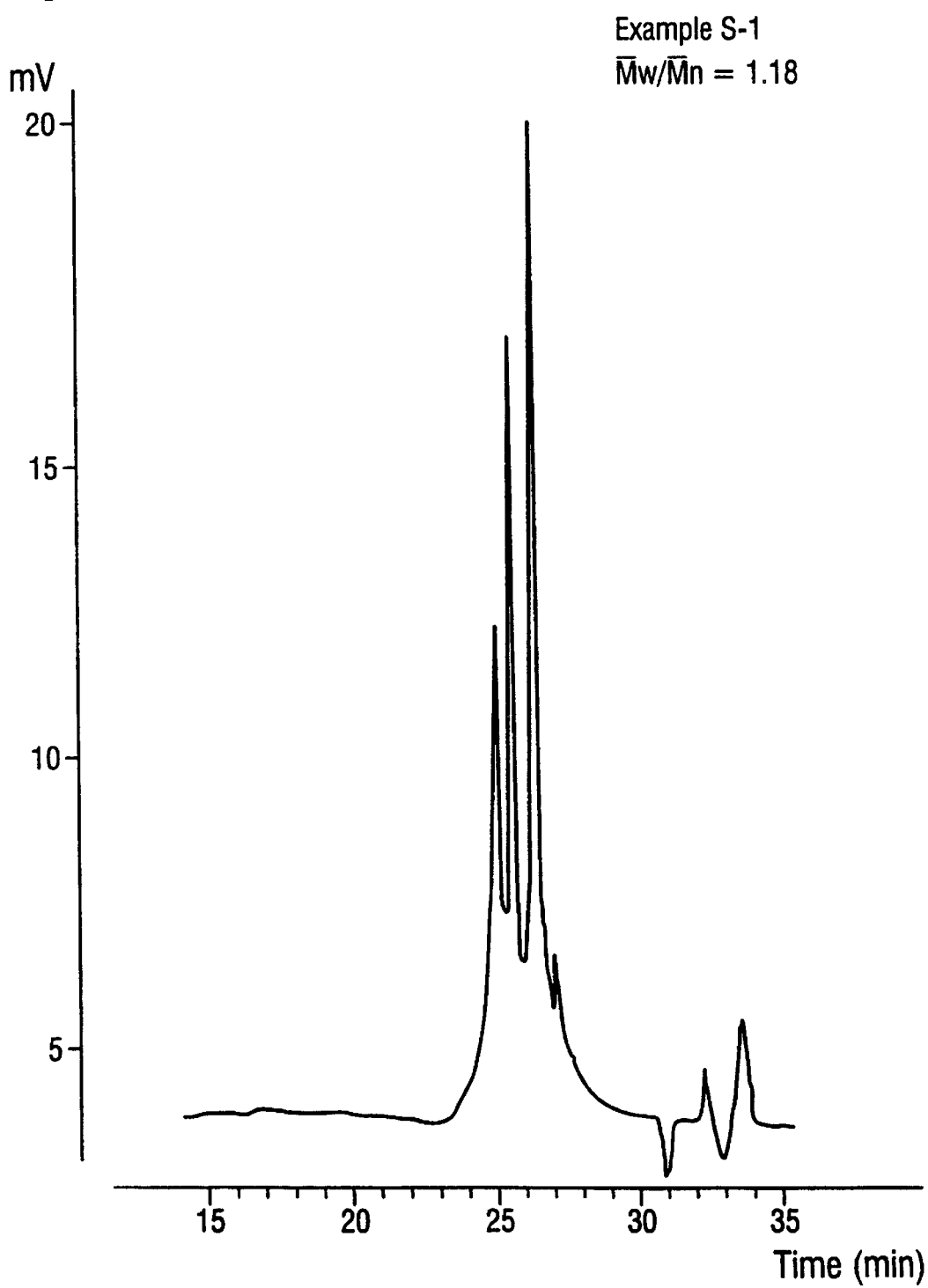

BLOCK OLIGOMERS CONTAINING 1-HYDROCARBYLOXY-2,2,6,6-TETRAMETHYL-4-PIPERIDYL GROUPS AS STABILIZERS FOR ORGANIC MATERIALS

The present invention relates to specific block oligomers containing 1-hydrocarbyloxy-2,2,6,6-tetramethyl-4-piperidyl groups, to their use as light stabilizers, heat stabilizers and oxidation stabilizers for organic materials, particularly synthetic polymers, and to the organic materials thus stabilized.

The stabilization of synthetic polymers with derivatives of 2,2,6,6-tetramethylpiperidine has been described for example in U.S. Pat. No. 4,086,204, 4,331,586, 4,335,242, 4,234,707, 4,459,395, 4,492,791, 5,204,473, EP-A-53 775, EP-A-357 223, EP-A-377 324, EP-A-462 069, EP-A-782 994 and GB-A-2 301 106.

The present invention relates in particular to a product obtainable by transferring groups of the formula (G-I)

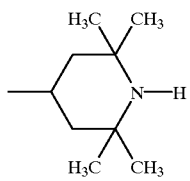

(G-I)

being present in a block oligomer having a polydispersity $\overline{M}w/\overline{M}n$ of 1 to 1.7 and corresponding to the formula (I)

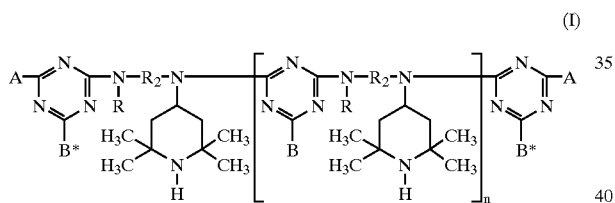

(I)

to groups of the formula (G-II);

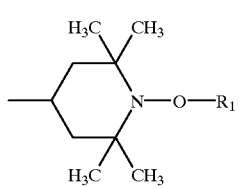

(G-II)

wherein $R_1$ is a hydrocarbyl radical or —O—$R_1$ is oxyl; said transfer is carried out by reaction of the block oligomer corresponding to the formula (I) with a hydroperoxide in a hydrocarbon solvent in the presence of a peroxide decomposing catalyst;

n is a number from 2 to 14;

the radicals $R_2$ are independently of one another $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi-($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_2$alkoxy)carbonyl or having one of the definitions of $R_4$ given below; or $R_2$ is a group of the formula (a), (b) or (c);

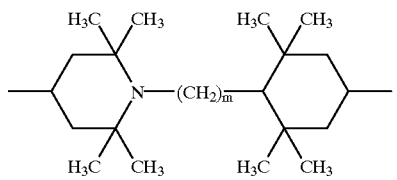

(a)

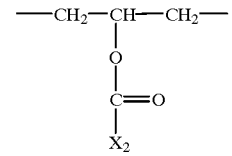

(b)

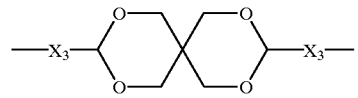

(c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene; the radicals A are independently of one another —$OR_3$, —$N(R_4)(R_5)$ or a group of the formula (II);

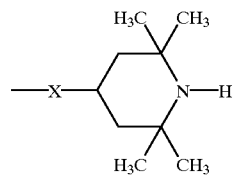

(II)

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

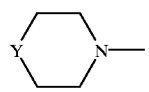

(III)

with Y being —O—, —$CH_2$—, —$CH_2CH_2$— or >N—$CH_3$;

and $R_3$ is additionally hydrogen or —$N(R_4)(R_5)$ is additionally a group of the formula (III);

X is —O— or >N—$R_6$;

$R_6$ is $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (G-I), or $C_2$–$C_4$alkyl which is substituted in the 2, 3 or 4 position by —OH, $C_1$–$C_8$alkoxy, di($C_1$–$C_4$alkyl)amino or a group of the formula (III);

the radicals R have independently of one another one of the meanings given for $R_6$; and the radicals B and B* have independently of one another one of the meanings given for A;

with the proviso that in the individual recurrent units of the formula (I), each of the radicals B, R and $R_2$ has the same or a different meaning.

In the repeating units of the formula (I), the radical R and the radical

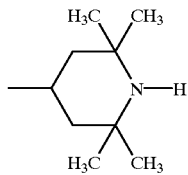

can have a random distribution or a block distribution.

The transfer of the groups of the formula (G-I) to groups of the formula (G-II) may be carried out, for example, analogously to the method described in U.S. Pat. No. 4,921,962 which is incorporated by reference herein.

Polydispersity indicates the molecular-weight distribution of a polymeric compound. In the present application, the polydispersity is the ratio of weight-average ($\overline{Mw}$) and number-average ($\overline{Mn}$) molecular weights. A value of $\overline{Mw}/\overline{Mn}$ equal to 1 means that the compound is monodispers and has only one molecular weight and no molecular weight distribution. A narrow molecular weight distribution is characterized by a polydispersity $\overline{Mw}/\overline{Mn}$ close to 1.

When the polydispersity $\overline{Mw}/\overline{Mn}$ is 1, n is preferably 2, 3, 4, 5, 6, 7, 8, 9, 10, 11 or 12, in particular 2, 3, 4, 5 or 6, for example 2, 4 or 6.

A preferred block oligomer of the formula (I) has a polydispersity $\overline{Mw}/\overline{Mn}$ of 1.1 to 1.7. Such a block oligomer is polydispers and has a molecular weight distribution. More specifically, such a block oligomer corresponds to a mixture containing at least three different monodispers compounds of the formula (I) which vary only by the variable n, said mixture having a polydispersity of 1.1 to 1.7.

When the polydispersity $\overline{Mw}/\overline{Mn}$ is higher than 1, n is preferably a number from 2 to 12, in particular 2 to 6.

Preferred block oligomers have a polydispersity $\overline{Mw}/\overline{Mn}$ of 1.1 to 1.65, 1.1 to 1.6, 1.1 to 1.55, 1.1 to 1.5, 1.1 to 1.45, 1.1 to 1.40 or 1.1 to 1.35. A polydispersity $\overline{Mw}/\overline{Mn}$ of 1.1 to 1.55, e.g. 1.1 to 1.5, is particularly preferred.

Further examples for the polydispersity $\overline{Mw}/\overline{Mn}$ are 1.15 to 1.7, for example 1.15 to 1.65, 1.15 to 1.6, 1.15 to 1.55, 1.15 to 1.5, 1.15 to 1.45, 1.15 to 1.40 or 1.15 to 1.35. A polydispersity $\overline{Mw}/\overline{Mn}$ of 1.15 to 1.55, e.g. 1.15 to 1.5, is also particularly preferred.

The meaning of $R_1$ depends on the hydrocarbon solvent used. $R_1$ is preferably a hydrocarbyl radical having 5 to 18 carbon atoms.

$R_1$ is in particular $C_5$–$C_{18}$alkyl, $C_5$–$C_{18}$alkenyl, $C_5$–$C_{18}$alkynyl, $C_5$–$C_{12}$cycloalkyl unsubstituted or substituted by $C_1$–$C_4$alkyl; $C_5$–$C_{12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl; and the hydrocarbon solvent is accordingly, dependent on $R_1$, $C_5$–$C_{18}$alkane, $C_5$–$C_{18}$alkene, $C_5$–$C_{18}$alkyne, $C_5$–$C_{12}$cycloalkane unsubstituted or substituted by $C_1$–$C_4$alkyl; $C_5$–$C_{12}$cycloalkene unsubstituted or substituted by $C_1$–$C_4$alkyl; a bicyclic or tricyclic hydrocarbon having 6 to 10 carbon atoms or $C_7$–$C_9$phenylalkane unsubstituted or substituted on the phenyl by $C_1$–$C_4$alkyl.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl. $R_1$ is preferably $C_6$–$C_{12}$alkyl, in particular heptyl or octyl. $R_4$, $R_5$ and $R_6$ are preferably $C_1$–$C_8$alkyl, in particular $C_1$–$C_4$alkyl.

An example of $C_2$–$C_4$alkyl substituted by —OH is 2-hydroxyethyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl) amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (111) is preferably

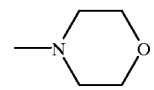

Preferred examples of $C_2$–$C_4$alkyl substituted by a group of the formula (III) are groups of the formula

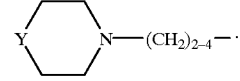

The group

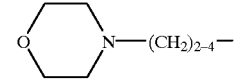

is particularly preferred.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

A preferred example of a bicyclic or tricyclic hydrocarbyl having 6 to 10 carbon atoms is 1,2,3,4-tetrahydronaphthenyl.

A preferred example of $C_5$–$C_{12}$cycloalkenyl unsubstituted or substituted by $C_1$–$C_4$alkyl is cyclohexenyl.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred, and allyl is particularly preferred.

A preferred example of $C_5$–$C_{18}$alkynyl is octynyl.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl which is unsubstituted or substituted on the phenyl by 1, 2 or 3 $C_1$–$C_4$alkyl are benzyl, methylbenzyl, dimethylbenzyl, trimethylbenzyl, t-butylbenzyl and 2-phenylethyl. Benzyl is preferred.

Examples of acyl (aliphatic, cycloaliphatic or aromatic) containing not more than 12 carbon atoms are formyl, acetyl, propionyl, butyryl, pentanoyl, hexanoyl, heptanoyl, octanoyl and benzoyl. $C_1$–$C_8$Alkanoyl and benzoyl are preferred. Acetyl is especially preferred.

Examples of ($C_1$–$C_{12}$alkoxy)carbonyl are methoxycarbonyl, ethoxycarbonyl, propoxycarbonyl, butoxycarbonyl, pentoxycarbonyl, hexoxycarbonyl, heptoxycarbonyl, octoxycarbonyl, nonyloxycarbonyl, decyloxycarbonyl, undecyloxycarbonyl and dodecyloxycarbonyl.

Examples of alkylene containing not more than 12 carbon atoms are ethylene, propylene, trimethylene, tetramethylene, pentamethylene, hexamethylene, octamethylene, decamethylene and dodecamethylene. $R_2$ is for example $C_2$–$C_8$alkylene or $C_4$–$C_8$alkylene, in particular $C_2$–$C_6$alkylene, preferably hexamethylene.

An example Of $C_1$–$C_{12}$alkenylene is 3-hexenylene.

An example of $C_5$–$C_7$cycloalkylene is cyclohexylene.

Examples of $C_4$–$C_{12}$alkylene interrupted by 1,4-piperazinediyl are

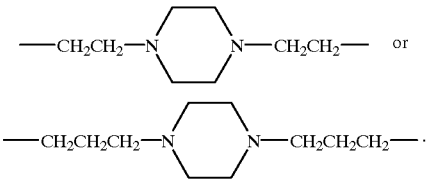

Examples of $C_4$–$C_{12}$alkylene interrupted by —O—, e.g. 1, 2 or 3—O—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

Examples of $C_4$–$C_{12}$alkylene interrupted by >N—$X_1$ are —$CH_2CH_2CH_2$—N($X_1$)—$CH_2CH_2$—N($X_1$)—$CH_2CH_2CH_2$—, in particular —$CH_2CH_2CH_2$—N($CH_3$)—$CH_2CH_2$—N($CH_3$)—$CH_2CH_2CH_2$—.

An example of $C_5$–$C_7$cycloalkylenedi($C_1$–$C_4$alkylene) is cyclohexylenedimethylene.

Examples of $C_1$–$C_4$alkylenedi($C_5$–$C_7$cycloalkylene) are methylenedicyclohexylene and isopropylidenedicyclohexylene.

An example of phenylenedi($C_1$–$C_4$alkylene) is phenylenedimethylene.

$R_1$ is preferably heptyl, octyl, cyclohexyl, methylcyclohexyl, cyclooctyl, cyclohexenyl, α-methylbenzyl or 1,2,3,4-tetrahydronaphthenyl, and the hydrocarbon solvent is accordingly, dependent on $R_1$, heptane, octane, cyclohexane, methylcyclohexane, cyclooctane, cyclohexene, ethylbenzene or tetralin.

According to a further preferred embodiment of this invention $R_1$ is cyclohexyl or octyl, and the hydrocarbon solvent is, dependent on $R_1$, cyclohexane or octane.

When —O—$R_1$ is oxyl, the hydrocarbon solvent is conveniently an inert organic solvent, preferably toluene or 1,2-dichloroethane.

The peroxide decomposing catalyst is, for example, a metal carbonyl, metal oxide, metal acetylacetonate or a metal alkoxide where the metal is selected from the groups IVb, Vb, VIb, VIIb and VII of the periodic table, preferably vanadium (III) acetylacetonate, cobalt carbonyl, chromium (VI) oxide, titanium (IV) isopropoxide, titanium tetrabutoxide, molybdenum hexacarbonyl, molybdenum trioxide and the like. The most preferred catalyst is $MoO_3$.

Suitable hydroperoxides are t-butyl hydroperoxide, t-amyl hydroperoxide, t-hexyl hydroperoxide, t-octyl hydroperoxide, ethylbenzene hydroperoxide, tetralin hydroperoxide or cumene (=isopropylbenzene) hydroperoxide. The most preferred hydroperoxide is t-butyl hydroperoxide.

2 to 8 moles, preferably 3 to 6 moles, of the hydroperoxide, 0.001 to 0.1 mole, preferably 0.005 to 0.05 moles, of the peroxide decomposing catalyst and 5 to 30 moles, preferably 10 to 20 moles, of the hydrocarbon solvent are applied, for example, per mole of the hindered amine moiety of the formula (G-I)

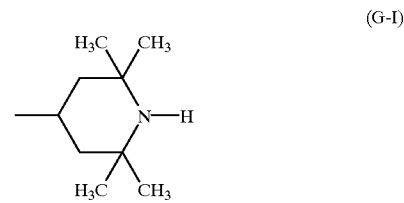

being present in the block oligomer.

The transfer of the hindered amine moieties of the formula (G-I) to groups of the formula

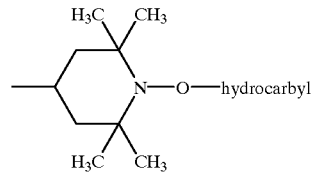

is, for example carried out at 75 to 160° C., preferably 100 to 150° C.

When the hindered amine moieties of the formula (G-I) are first treated with aqueous hydroperoxide in the presence of the peroxide decomposing catalyst in an inert organic solvent (for example analogously to the method described in U.S. Pat. No. 4,691,015), the initial reaction product obtained in a relatively short time is the corresponding N-oxyl intermediate (—OR, =oxyl) which is highly colored and which can be isolated per se.

When the organic solvent is a hydrocarbon having a labile hydrogen atom, when there remains a sufficient molar excess of hydroperoxide beyond that needed to convert the amine to the corresponding N-oxyl derivative, and when the reaction mixture is heated at moderate temperatures (preferably 100 to 150° C.) for an additional period, a further reaction takes place between the N-oxyl compound (either prepared in situ from the original amine or employed as the initial starting intermediate in the process) and the hydrocarbon solvent to give the corresponding N-hydrocarbyloxy derivative.

The original reaction mixture is colorless, but becomes highly colored as the N-oxyl intermediate is formed. This color disappears as the N-oxyl compound is converted into the colorless N-hydrocarbyloxy product. This process thus in essence has a built-in color indicator to show the extent of reaction. When the reaction mixture becomes colorless, it shows that the colored N-oxyl intermediate has been completely converted into the N-hydrocarbyloxy product.

If desired, the product according to this invention can be purified by one of the following methods:

a) Residual peroxide is decomposed and solvent is evaporated to obtain a crude solid product. The solid is stirred with an inert solvent such as cyclohexane, octane, hexane, petroleum ether, xylene, toluene, acetone, methyl ethyl ketone, ethyl acetate, butyl acetate, t-butyl alcohol, t-amyl alcohol, isopropyl alcohol, ethanol, methanol, chloroform, dichloromethane, acetonitrile, diethyl ether, dibutyl ether and/or water. The mixture may be heated while stirring. After stirring, the mixture is cooled and the solid product is collected by filtration and dried.

b) Residual peroxide is decomposed and solvent is partially evaporated. The residue is filtered to obtain a solid which is washed with an inert solvent such as one of the above, which may be chilled, and then dried.

c) Residual peroxide is decomposed and solvent is evaporated at elevated temperature to obtain a melt. The warm melt is mixed with an inert solvent, such as one of the above, which may be chilled, and the resulting precipitate is collected by filtration and dried. Variations of this procedure include mixing the warm melt with solvent and then cooling the mixture to obtain a precipitate, or mixing the warm melt with solvent, heating to bring any solids into solution, and then cooling to obtain a precipitate.

d) Residual peroxide is decomposed and solvent is evaporated at elevated temperature to obtain a melt. The melt is dissolved in an inert solvent, such as one of the above, with or without heating, and the resulting solution may be concentrated by distilling off some of the excess solvent. The solution is then mixed with a second solvent, such as one of the above, at a temperature such that the product precipitates. The solid is collected by filtration and dried.

More Specifically the Product According to This Invention is Preferably Purified as Follows After the reaction is complete, the crude reaction mixture is cooled to 50° C. and treated with 20% aqueous sodium sulfite until the concentration of residual peroxide falls below 0.5%. The aqueous layer is split off, and the organic layer is concentrated by heating the product solution at reduced pressure. The crude product is dissolved in excess t-butyl alcohol, and solvent is removed by heating the solution at reduced pressure until the concentration of solids is 50%. This solution is slowly added to cold methanol. The resulting precipitate is filtered, washed with methanol, and dried by heating under vacuum.

The block oligomer starting material of the formula (I) having a polydispersity of 1 to 1.7 is described in U.S. patent application Ser. No. 08/756,225 and in EP-A-782,994.

A block oligomer starting material having a polydispersity $\overline{M}w/\overline{M}n$ of a value higher than 1 to a value of 1.7 may be prepared, for example, as follows:

1) reacting a compound of the formula (A)

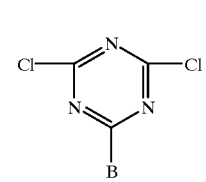

(A)

with a compound of the formula (B)

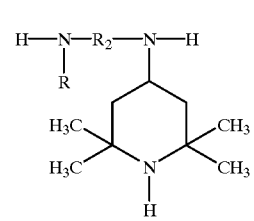

(B)

in a stoichiometric ratio to obtain a compound of the formula (C);

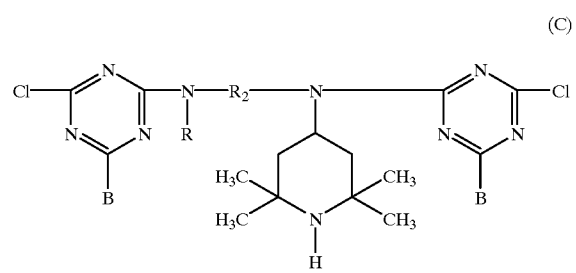

(C)

2) reacting a compound of the formula (C) with a compound of the formula (B) in a molar ratio of 1:2 to 1:3, preferably 1:2, to obtain a mixture of at least three different monodispers compounds of the formula (D) with n being 2, 3, 4, 5, 6, 7, 8, 9, 10, 11, 12, 13 or 14, in particular 2, 4 and 6;

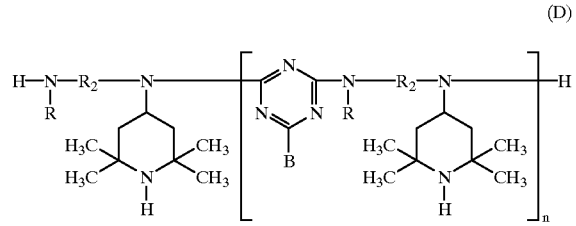

(D)

3) reacting the mixture obtained in 2) with a compound of the formula (E)

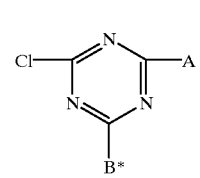

(E)

in a stoichiometric ratio to obtain the desired product with the indicated polydispersity; the reactions 1) to 3) being carried out in an organic solvent in the presence of an inorganic base.

Examples for suitable organic solvents are toluene, xylene, trimethylbenzene, isopropylbenzene, diisopropylbenzene and essentially water-insoluble organic ketones such as for example methyl ethyl ketone and methyl isobutyl ketone. Xylene is preferred.

Examples for an inorganic base are sodium hydroxide, potassium hydroxide, sodium carbonate and potassium carbonate. Sodium hydroxide is preferred.

The reaction 1) is carried out, for example, at a temperature of 40° C. to 70° C., preferably 50° C. to 60° C.

The reaction 2) is carried out, for example, at a temperature of 110° C. to 180° C., preferably 140° C. to 160° C.

The reaction 3) is carried out, for example, at a temperature of 110° C. to 180° C., preferably 140° C. to 160° C.

Possible by-products are the compounds of the formulae (B-I) and (B-II).

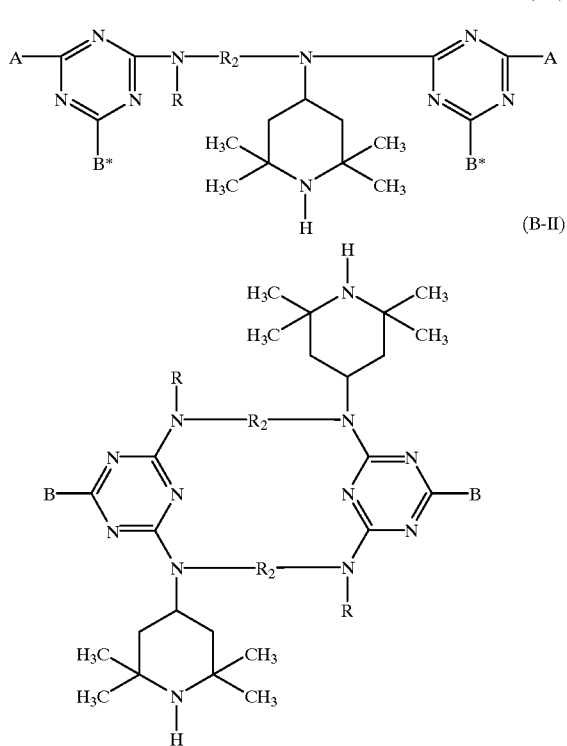

Each of these compounds which are known from U.S. Pat. No. 4,108,829 and 4,442,250 may be present in the mixtures in an amount of, for example, up to 30 mol %, preferably up to 20 mol % or up to 10 mol %, in particular up to 8 mol %, relative to the total mixture.

The compound of the formula (A) can be prepared, for example, by reacting cyanuric chloride with a compound B—H in a stoichiometric ratio in the presence of an organic solvent and an inorganic base.

Furthermore, the compound of the formula (E) can be prepared, for example, by reacting cyanuric chloride with compounds of the formulae A—H and B*—H in a stoichiometric ratio in the presence of an organic solvent and an inorganic base.

It is appropriate to use for the preparation of the compounds of the formulae (A) and (E) the same solvent and the same inorganic base than in the above indicated reactions 1) to 3). The starting materials used in the above process are known. In the case that they are not commercially available, they can be prepared analogously to known methods. For example, some starting materials of the formula (B) are described in WO-A-95/21157, U.S. Pat. No. 4,316,837 and 4,743,688.

A particularly preferred starting material is a product having a polydispersity $\overline{M}w/\overline{M}n$ of 1.1 to 1.7 or more specifically a mixture with the indicated polydispersity, said mixture containing at least three monodispers compounds which differ only by the number of the repetitive units and which are a) a compound of the formula (S-Ia)

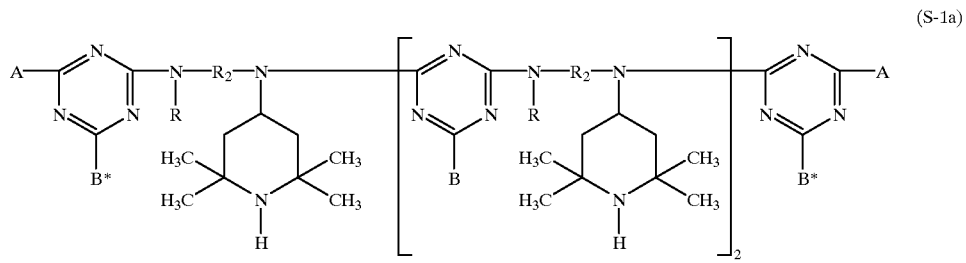

b) a compound of the formula (S-Ib) and

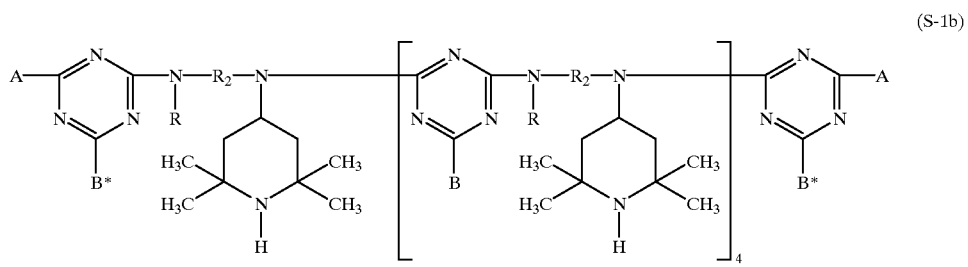
(S-1b)

c) a compound of the formula (S-Ic),

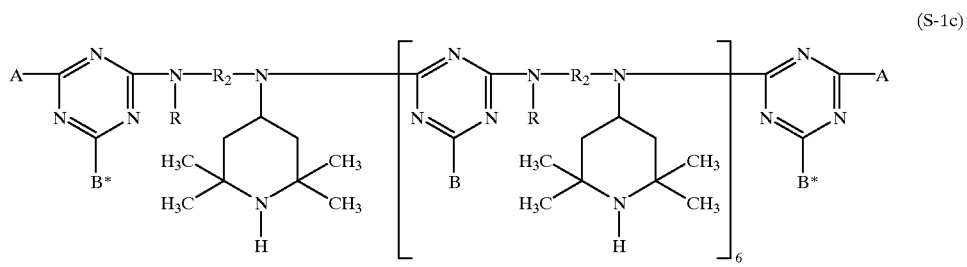
(S-1c)

the radicals A, B, B*, R and $R_2$ are as defined above and the ratio of the compounds of the formula (S-Ia) to (S-Ib) to (S-Ic) in molar % is 2:1.6:1 to 2:0.4:0.04, preferably 2:1.2:0.5 to 2:0.4:0.04, in particular 2:1:0.4 to 2:0.45:0.04.

Starting materials of the formula (I) having a polydispersity $\overline{M}w/\overline{M}n$ of 1 may be prepared by building up said compound step by step. Some representative examples for such a procedure are shown below.

I) A compound of the formula (I) wherein R is a group of the formula (G-I) and n is 2 may conveniently be prepared by reacting a compound of the formula (E) with a large excess of a compound of the formula (B) to obtain a compound of the formula (F) according to Scheme I-1. The molar ratio of the compound of the formula (E) to the compound of the formula (B) may be for example 1:4.

Scheme I-1

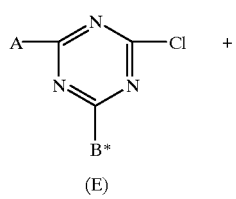
(E)

-continued

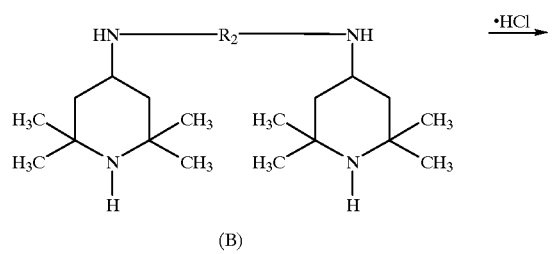
(B)

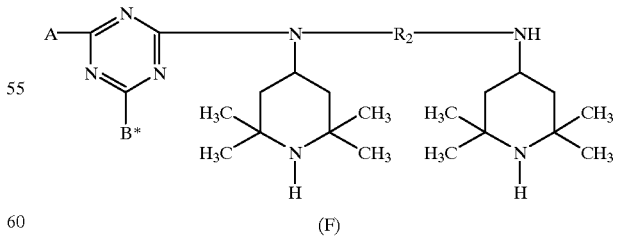
(F)

Subsequently, the compound of the formula (F) may be reacted with the compound of the formula (C) in a stoichiometric ratio to obtain the desired compound as shown in Scheme I-2.

Scheme I-2

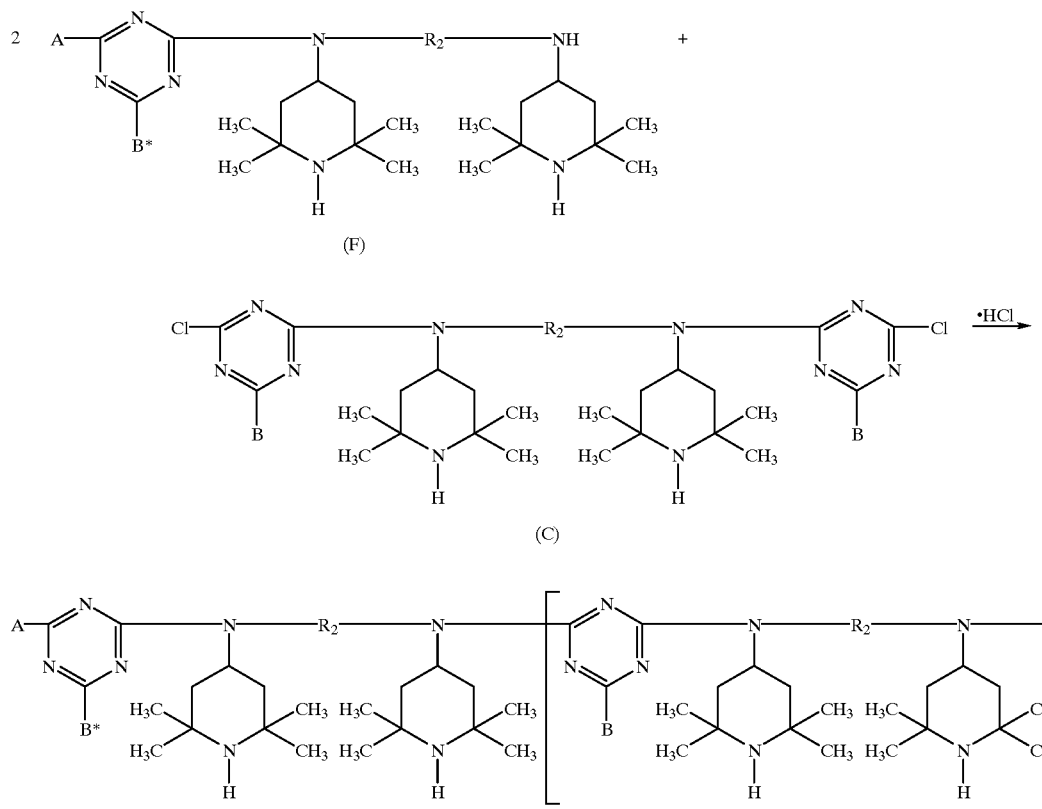

II) A compound of the formula (I) wherein R is a group of the formula (G-I) and n is 3 may conveniently be prepared by reacting a compound of the formula (F) with a compound of the formula (A) in a stoichiometric ratio to obtain a compound of the formula (G) according to Scheme II-1.

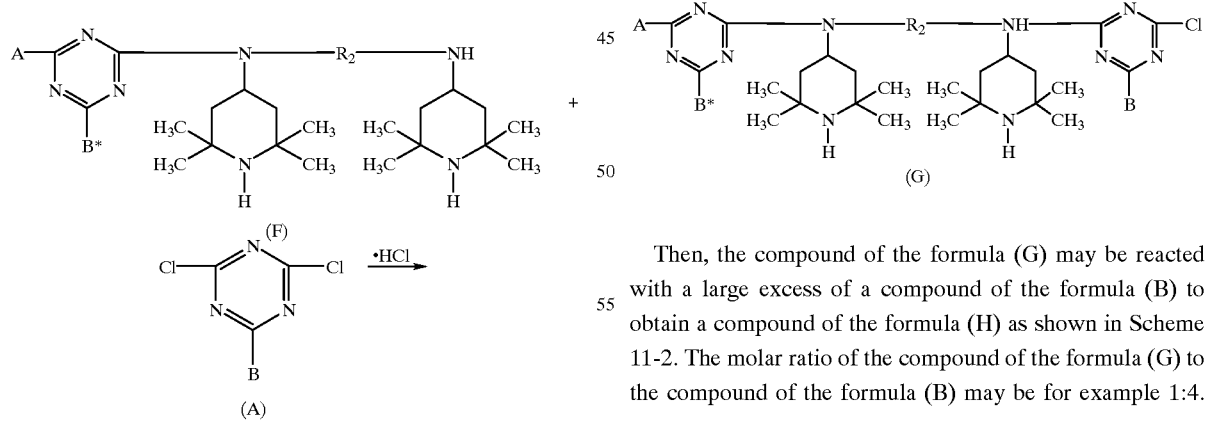

Then, the compound of the formula (G) may be reacted with a large excess of a compound of the formula (B) to obtain a compound of the formula (H) as shown in Scheme 11-2. The molar ratio of the compound of the formula (G) to the compound of the formula (B) may be for example 1:4.

Scheme II-2
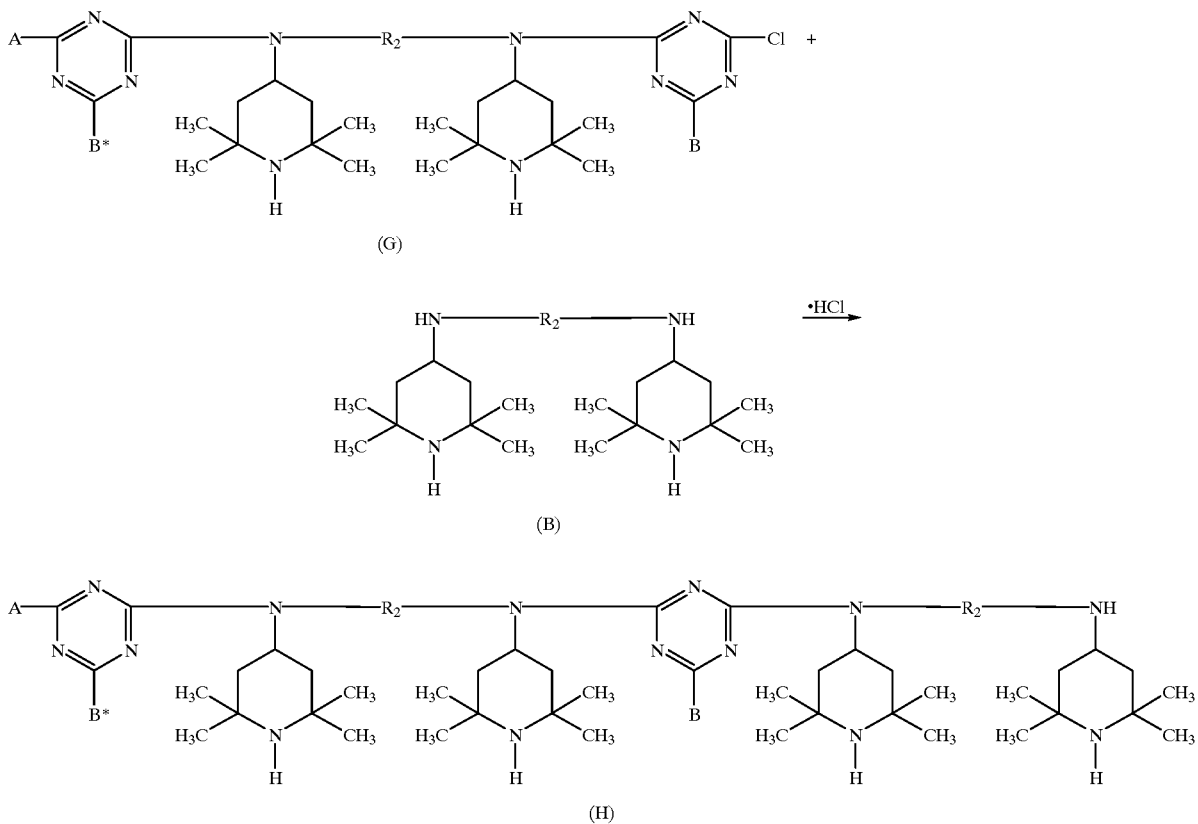
Subsequently, the compound of the formula (H) may be reacted with a compound of the formula (A) in a stoichiometric ratio to obtain a compound of the formula (K), following the Scheme 11-3.
Scheme II-3
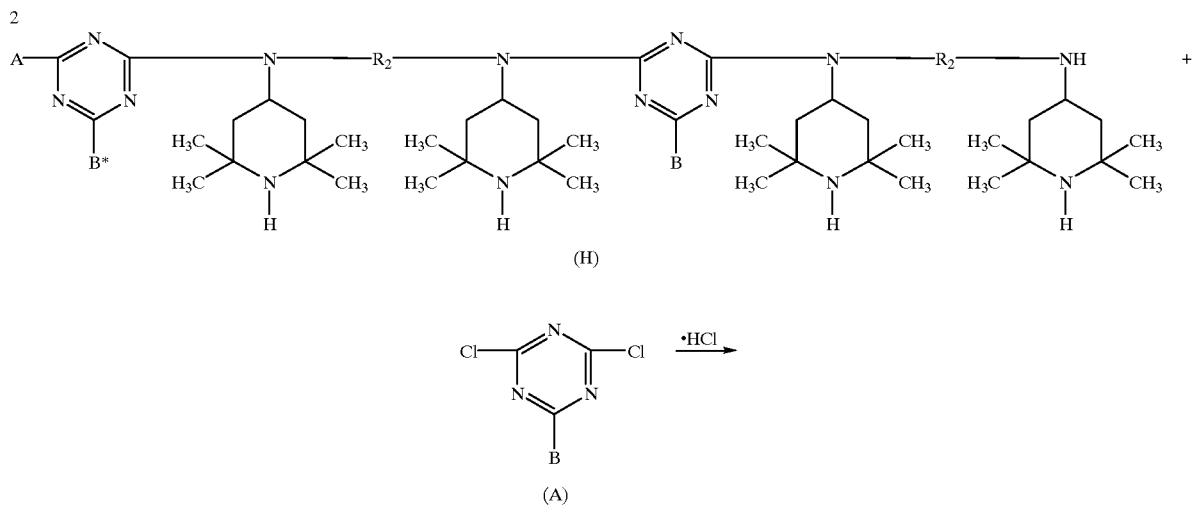

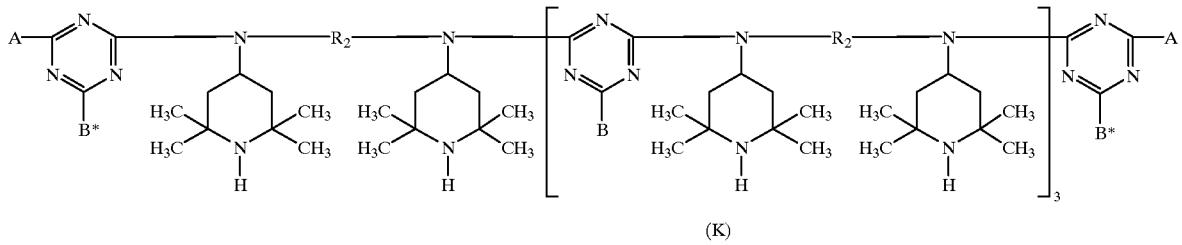

(K)

III) A compound of the formula (I) wherein R is a group of the formula (G-I) and n is 4 may conveniently be prepared by reacting a compound of the formula (H) with a compound of the formula (C) in a stoichiometric ratio to obtain a compound of the formula (L).

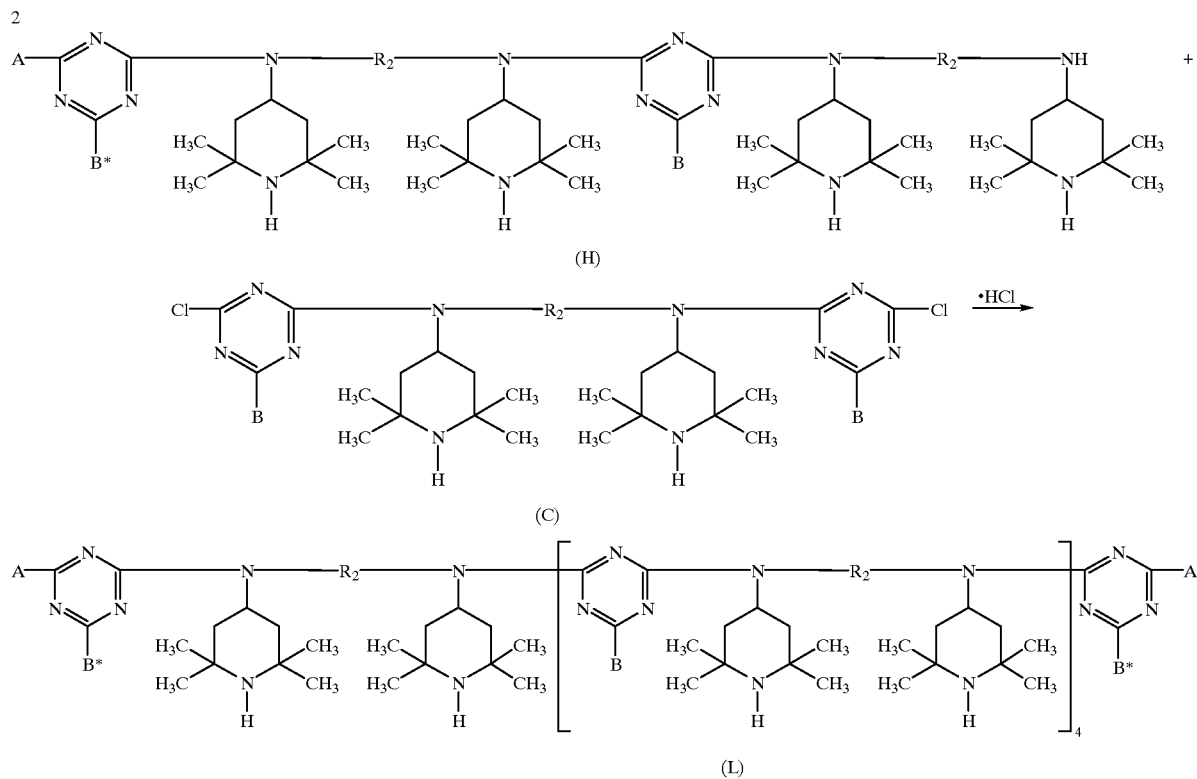

The reactions I) to III) are carried out, for example, in an organic solvent such as toluene, xylene, trimethylbenzene in the presence of an inorganic base such as sodium hydroxide at a temperature of 110° C. to 180° C., preferably 140° C. to 160° C.

Preferred products of this invention are those, wherein R is a group of the formula (G-I).

Preferred products of this invention are also those, wherein $R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by —O— or >N—$X_1$ with $X_1$ being $C_1$–$C_{12}$acyl or ($C_1$–$C_{12}$alkoxy)carbonyl or having one of the definitions of $R_4$; or $R_2$ is a group of the formula (b);

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl;

and $R_3$ is additionally hydrogen or —N($R_4$)($R_5$) is additionally a group of the formula (III);

$R_6$ is $C_1$–$C_{18}$alkyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; or a group of the formula (G-I).

A further preferred embodiment of this invention relates to those products, wherein n is a number from 2 to 12;

$R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$alkylene);

$R_6$ is $C_1$–$C_{18}$alkyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; or a group of the formula (G-I); and R is a group of the formula (G-I).

Those products are of interest, wherein $R_2$ is $C_2$–$C_{10}$alkylene, cyclohexylene, cyclohexylenedi($C_1$–$C_4$alkylene), $C_1$–$C_4$alkylene-dicyclohexylene or phenylenedi($C_1$–$C_4$alkylene);

$R_3$, $R_4$ and $R_5$, which are identical or different, are $C_1$–$C_{12}$alkyl, $C_5$–$C_7$cycloalkyl which is unsubstituted or substituted by 1, 2 or 3 $C_1$–$C_4$alkyl; phenyl which is unsubstituted or substituted by 1, 2 or 3 $C_1$–$C_4$alkyl; or benzyl which is unsubstituted or substituted on the phenyl by $C_1$–$C_4$alkyl; or —N($R_4$)($R_5$) is additionally a group of the formula (III); and $R_6$ is $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; or a group of the formula (G-I).

Also of interest are those products, wherein $R_2$ is $C_2$–$C_8$alkylene;

$R_3$, $R_4$ and $R_5$, which are identical or different, are $C_1$–$C_8$alkyl, cyclohexyl which is unsubstituted or substituted by methyl; phenyl which is unsubstituted or substituted by methyl; or benzyl; or —N($R_4$)($R_5$) is additionally 4-morpholinyl; and $R_6$ is $C_1$–$C_8$alkyl, cyclohexyl which is unsubstituted or substituted by methyl; benzyl or a group of the formula (G-I).

Of further interest is a product, wherein n is a number from 2 to 6;

$R_2$ is $C_2$–$C_6$alkylene;

A is —N($R_4$)($R_5$) or a group of the formula (II);

$R_4$ and $R_5$, which are identical or different, are $C_1$–$C_8$alkyl; or —N($R_4$)($R_5$) is additionally 4-morpholinyl;

X is >N$R_6$;

$R_6$ is $C_1$–$C_4$alkyl; and the radicals B and B* have independently of one another one of the definitions given for A.

A further preferred product is that, wherein B* is different from B and each of the radicals B, R and $R_2$ has the same meaning in the individual recurring units of the formula (I).

An embodiment of this invention is also a product obtainable by hydrogenating a product wherein —OR, in the formula (G-II) is oxyl to obtain a block oligomer with groups of the formula (G-III).

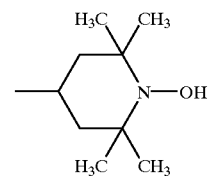

(G-III)

The hydrogenation is carried out according to known methods, for example in an organic solvent, e.g. methanol or ethanol, in the presence of a hydrogenation catalyst, preferably palladium on carbon or PtO$_2$, as described e.g. in U.S. Pat. No. 4,691,015.

Another embodiment of this invention is a mixture containing a) a monodispers compound of the formula (Ia),

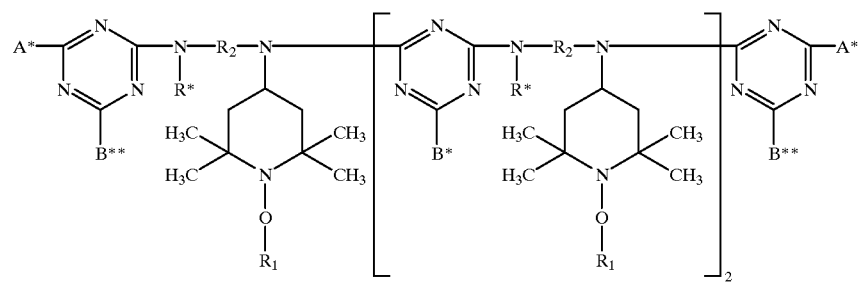

(Ia)

b) a monodispers compound of the formula (Ib) and

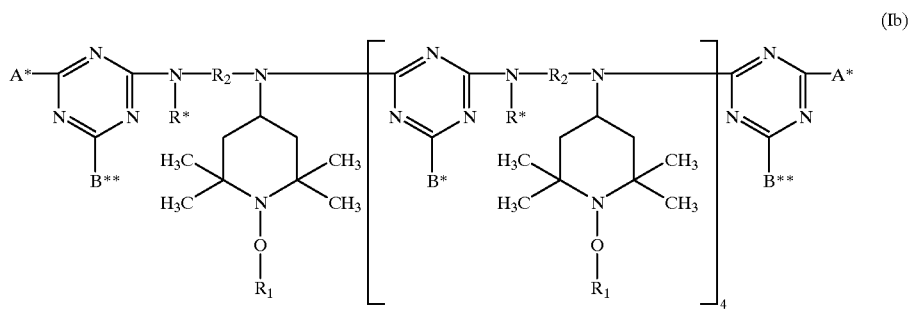

(Ib)

c) a monodispers compound of the formula (Ic)

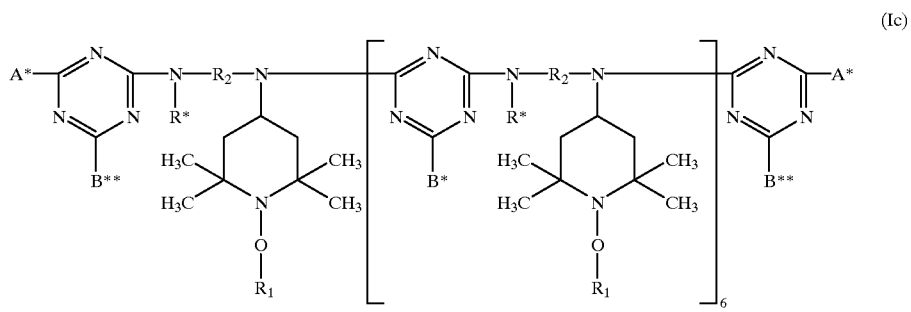

(Ic)

the compounds of the formulae (Ia), (Ib) and (Ic) differ only in the number of the repetitive units, the ratio of the compounds of the formula (Ia) to (Ib) to (Ic) in molar % is 2:1.6:1 to 2:0.4:0.04, preferably 2:1.2:0.5 to 2:0.4:0.04, in particular 2:1:0.4 to 2:0.45:0.04; and $R_1$ is hydrogen, a hydrocarbyl radical or —O—R, is oxyl;

$R_2$ is $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi-($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below; or $R_2$ is a group of the formula (a), (b) or (c);

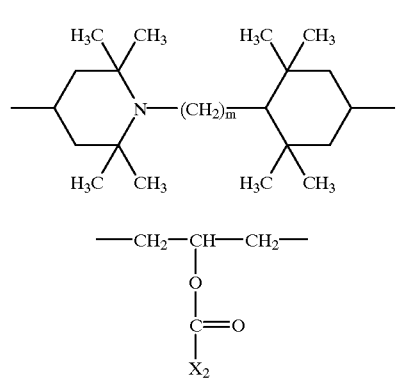

(a)

(b)

-continued (c)

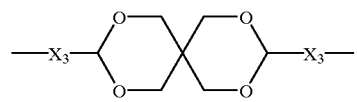

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

$A^*$ is —$OR_3$, —$N(R_4)(R_5)$ or a group of the formula (G-IV);

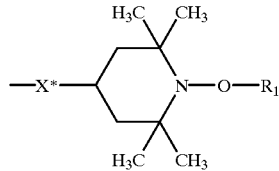

(G-IV)

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

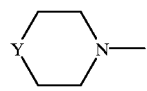

(III)

with Y being —O—, —CH$_2$—, —CH$_2$CH$_2$— or >N—CH$_3$;
and $R_3$ is additionally hydrogen or —N($R_4$)($R_5$) is additionally a group of the formula (III); X* is —O— or >N—$R_6$*;
$R_6$* is $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (G-II),

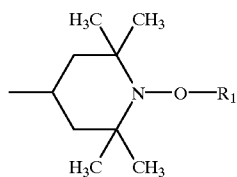

(G-II)

or $C_2$–$C_4$alkyl which is substituted in the 2, 3 or 4 position by —OH, $C_1$–$C_8$alkoxy, di($C_1$–$C_4$alkyl)amino or a group of the formula (III);
R* has one of the meanings given for $R_6$*; and
the radicals B* and B** have independently of one another one of the meanings given for A*.
After the transfer of the groups of the formula (G-I)

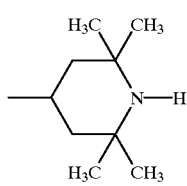

(G-I)

being present in a block oligomer starting material with a polydispersity of, for example, 1.1 to 1.7 (mixture containing the compounds of the formulae (S-Ia), (S-Ib) and (S-Ic)) to groups of the formula (G-II),

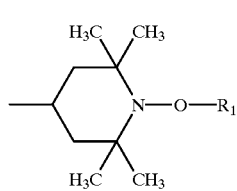

(G-II)

the ratio of the compounds of the formula (Ia) to (Ib) to (Ic) corresponds to the ratio of the above shown initial compounds of the formula (S-Ia) to (S-Ib) to (S-Ic), since the backbone of these compounds is not affected during the reaction.

Preferred is a mixture, wherein
$R_1$ is cyclohexyl or octyl;
$R_2$ is $C_2$–$C_6$alkylene;
A* and B** which are identical or different are —N($C_1$–$C_8$alkyl)$_2$ or a group of the formula (G-IV-1)

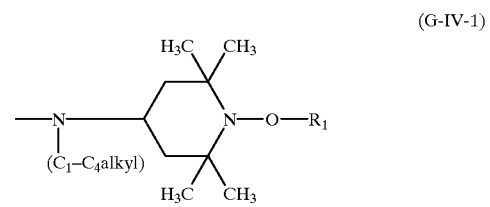

(G-IV-1)

B* is a group of the formula (G-IV-1); and
R* is a group of the formula (G-I1).

In the mixtures according to this invention, the radical $R_1$ can act as a linking group between two or more block oligomers of the formula (Ia), (Ib) and/or (Ic). In this case, bridges of the formula (L-I) are formed

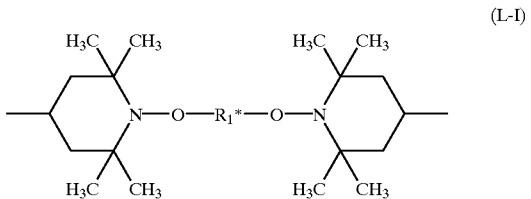

(L-I)

between the indicated block oligomers.

The meaning of $R_1$* can be deduced from the meaning of $R_1$. The only difference between these two radicals is that $R_1$* has one or two additional valences. Thus, $R_1$ as cyclohexyl corresponds to $R_1$* as cyclohexanediyl or cyclohexanetriyl and $R_1$ as octyl corresponds to $R_1$* as octanediyl or octanetriyl.

The products of this invention as well as the described mixtures are very effective in improving the light, heat and oxidation resistance of organic materials, especially synthetic polymers and copolymers. In particular, a low pigment interaction as well as a very good colour is observed in polypropylene, especially polypropylene fibres, in particular in the presence of flame retardants as well as in low density polyethylene (LDPE) films for agricultural uses. It is further remarkable that the product of this invention and the described mixtures are flame retardants themselves.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VII of the Periodic Table. These metals usually have one or more than one ligand, typically oxides, halides, alcoholates, esters, ethers, amines, alkyls, alkenyls and/or aryls that may be either π- or σ-coordinated.

These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-i-ene copolymers, propylene/isobutylene copolymers, ethylene/but-i-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EM), LLDPE/EVA, LLDPE/EM and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyIsocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polylmides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyIsocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose pro-pionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PANPP, PA/PPO, PBT/PC/ABS or PBT/PET/PC.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

The invention thus also relates to a composition comprising an organic material susceptible to degradation induced by light, heat or oxidation and a product or a mixture according to this invention.

The organic material is preferably a synthetic polymer, more particularly one selected from the aforementioned groups. Polyolefins are preferred and polyethylene and polypropylene are particularly preferred.

A further embodiment of this invention is a method for stabilizing an organic material against degradation induced by light, heat or oxidation, which comprises incorporating into said organic material a product or a mixture according to this invention.

The product or the mixture according to this invention can be used in various proportions depending on the nature of the material to be stabilized, on the end use and on the presence of other additives.

In general, it is appropriate to use, for example, 0.01 to 5% by weight of the product or the mixture according to this invention, relative to the weight of the material to be stabilized, preferably 0.05 to 2%, in particular 0.05 to 1%.

The product or the mixture according to this invention can be added, for example, to the polymeric materials before, during or after the polymerization or crosslinking of the said materials. Furthermore, it can be incorporated in the polymeric materials in the pure form or encapsulated in waxes, oils or polymers.

In general, the product or the mixture according to this invention can be incorporated in the polymeric materials by various processes, such as dry mixing in the form of powder, or wet mixing in the form of solutions or suspensions or also in the form of a masterbatch which contains the product or the mixture according to this invention in a concentration of 2.5 to 25% by weight; in such operations, the polymer can be used in the form of powder, granules, solutions, suspensions or in the form of latices.

The materials stabilized with the product or the mixture according to this invention can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the product or the mixture according to this invention.

Particular examples of said conventional additives are:
1. Antioxidants
1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-di-methyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, - bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4 -hydroxyphenylpropionyl)-hexahydro-1,3,5-triazine, 1,3,5-tris(3,5-dicyclohexyl-4-hydroxybenzyl) isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamine, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylpheno thiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl (α-cyano-p-methyl-β-methoxy-cinnamate, methyl α-carbomethoxy-p- methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethyipiperidyl)succinate, linear or cyclic condensates of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl- 4-piperidyl)pyrrolidin-2,5-dione, 3-dodecyl-1-(1,2,2,6,6-pentamethyl-4-piperidyl)pyrroidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxymethylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3 -butoxy-2-hydroxy-propoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis (salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,6-di-tertbutyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl))pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methyl phosphite, bis(2,4-di-tert-butyl-6-methylphenyl) ethyl phosphite, 2,2',2''-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatechotate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butylbenzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The weight ratio of the product or the mixture according to this invention to the conventional additives may be, for example, 1:0.5 to 1:5.

The products or mixtures of this invention can also be used as stabilizers, especially as light stabilizers, for almost all materials known in the art of photographic reproduction and other reproduction techniques as e.g. described in Research Disclosure 1990, 31429 (pages 474 to 480).

The invention is illustrated in more detail by the following Examples. All percentages and parts are by weight, unless otherwise indicated.

The following Examples S-1 and S-2 are representative for the preparation of the starting materials. Examples 1 to 4 are representative for the preparation of the products according to this invention.

GPC (Gel Permeation Chromatography) is used as an analytical procedure for separating molecules by their difference in size and to obtain molecular weight averages($\overline{Mw}$, $\overline{Mn}$) or information on the molecular weight distribution of polymers.

The technique is well known and described, for instance, in "Modern Size—Exclusion Liquid Chromatography" by W. W. Yan et al., edited by J. Wiley & Sons, N.Y., USA, 1979, pages 4–8, 249–283 and 315–340.

A narrow molecular weight distribution is characterized by a polydispersity ($\overline{Mw}/\overline{Mn}$) close to 1.

The GPC analyses shown in the following Examples S-1 and S-2 are carried out with a GPC chromatograph ®Perkin-Elmer LC 250 equipped with ®Perkin-Elmer RI detector LC 30 and with ®Perkin-Elmer oven LC 101.

All the analyses are carried out at 45° C by using three columns PLGEL 3 μm Mixed E 300 mm length×7.5 mm i.d.(from Polymers Laboratories Ltd. Shropshire, U.K).

Tetrahydrofurane is used as eluant (flow 0.40 ml/min) and the samples are dissolved in tetrahydrofurane (2%) (% w/v).

In the structural formulae of the following examples, n' indicates that there are repetitive units in the molecules and the products obtained are not uniform.

EXAMPLE S-1

Preparation of the Product of the Formula

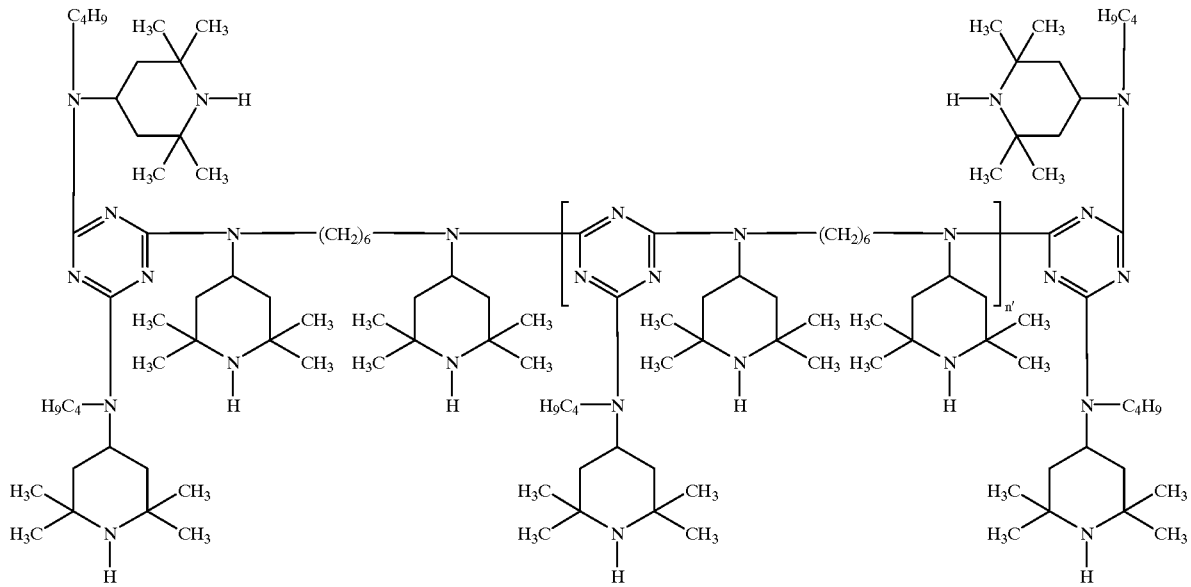

A solution of 74.3 g (0.35 moles) of N-(2,2,6,6-tetramethyl-4-piperidinyl)-n-butylamine in 50 ml of water is added slowly, at 0° C. to a solution of 64.5 g (0.35 moles) of cyanuric chloride in 500 ml of xylene, keeping the temperature during the addition and for further 1 hour.

After 2 hours at room temperature the mixture is cooled to 0° C. and an aqueous solution of 14.7 g (0.368 moles) of sodium hydroxide in 50 ml of water is added. After ½ hour at 0C and further 2 hours at room temperature, the aqueous solution is separated off and 69.2 g (0.175 moles) of N,N'-bis(2,2,6,6-tetramethyl-4-piperidinyl)-1,6-hexanediamine are added.

The mixture is heated to 50° C. for 1 hour and 48.4 g (0.35 moles) of ground potassium carbonate are added and heated to 60° C. for 4 hours.

After washing with water, the organic phase is concentrated under vacuum at 60–70° C./1 0 mbar, being 250 ml of xylene recovered.

138.1 g (0.35 moles) of N,N'-bis(2,2,6,6-tetramethyl-4-piperidinyl)-1,6-hexanediamine are added and the mixture is heated to 150° C. for 2 hours, cooled again and added with 14 g (0.35 moles) of ground sodium hydroxide.

The mixture is heated to 140° C. for further 4 hours, being the residual water of reaction eliminated off azeotropically and for further 4 hours at 160° C.

After cooling to 60° C., the mixture is diluted with 300 ml of xylene, filtered and washed three times with 100 ml of ethylene glycol.

After concentrating under vacuum at 60° C./10 mbar 78.7 g (0.147 moles) of 2-chloro-4,6-bis[N-(2,2,6,6-tetramethyl-4-piperidinyl)-n-butylamino)-1,3,5-triazine are added.

The mixture is heated to 140° C. for 3 hours and 5.9 g (0.147 moles) of ground sodium hydroxide are added, being the mixture heated to reflux and being the reaction water eliminated off azeotropically.

The mixture is heated to 160° C. for 4 hours, added with further 5.9 9 (0.147 moles) of ground sodium hydroxide and heated again to 160° C. for 2 hours.

After cooling to 60° C., the mixture is diluted with 300 ml of xylene, filtered and concentrated under vacuum at 140° C./1 mbar.

A solid is obtained with a melting range of 166–170° C./after drying.

$\overline{Mn}$ (by GPC): 3360 g/mol

Polydispersity $\overline{Mw}/\overline{Mn}$: 1.18

The GPC analysis shows a chromatogram as in FIG. 1.

The ratio of the three main single components ((n'=2):(n'=4):(n'=6)) of the polydispers product obtained is in molar % 2:0.53:0.05.

EXAMPLE S-2

Preparation of the Product of the Formula

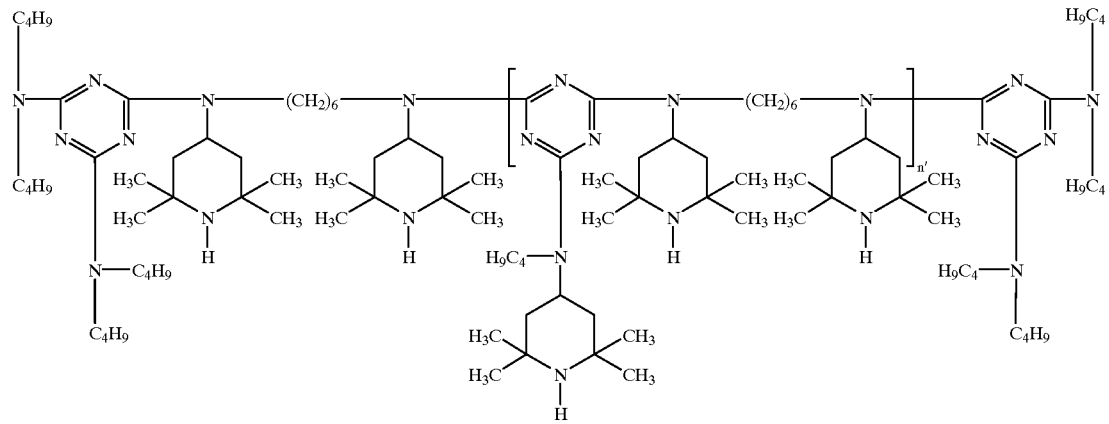

A solution of 74.3 g (0.35 moles) of N-(2,2,6,6-tetramethyl-4-piperidinyl)-n-butylamine in 50 ml of water is added slowly at 0° C. to a solution of 64.5 g (0.35 moles) of cyanuric chloride in 500 ml of xylene, keeping the temperature during the addition and for further 1 hour.

After 2 hours at room temperature, the mixture is cooled to 0° C. and an aqueous solution of 14.7 g (0.368 moles) of sodium hydroxide in 50 ml of water is added.

After ½ hour at 0° C. and for further 2 hours at room temperature, the aqueous solution is separated off and 69.2 g (0.175 moles) of N,N'-bis(2,2,6,6-tetramethyl-4-piperidinyl)-1,6-hexanediamine are added.

The mixture is heated to 50° C. for 1 hour and 48.4 g (0.35 moles) of ground potassium carbonate are added and heated to 60° C. for 4 hours.

After washing with water, the organic phase is concentrated under vacuum at 60–70° C./10 mbar, being 250 ml of xylene recovered.

138.1 9 (0.35 moles) of N,N'-bis(2,2,6,6-tetramethyl-4-piperidinyl)-1,6-hexanediamine are added and the mixture is heated to 150° C. for 2 hours, cooled again and added with 14 g (0.35 moles) of ground sodium hydroxide.

The mixture is heated to 140° C. for further 4 hours, being the residual water of reaction eliminated off azeotropically and for further 4 hours at 160° C.

After cooling to 60° C., the mixture is diluted with 300 ml of xylene, filtered and washed three times with 100 ml of ethylene glycol.

After concentrating under vacuum at 60° C./10 mbar, 54.4 g (0.147 moles) of 2-chloro-4,6-bis-(dibutylamino)-1,3,5-triazine are added.

The mixture is heated to 140° C. for 3 hours and 20.3 g (0.147 moles) of ground potassium carbonate are added, being the mixture heated to reflux and being the reaction water eliminated off azeotropically.

The mixture is heated to 160° C. for 4 hours, added to further 20.3 g (0.147 moles) of ground potassium carbonate and heated again to 160° C. for 2 hours. After cooling to 60° C., the mixture is diluted with 300 ml of xylene, filtered and concentrated under vacuum at 140° C.11 mbar.

A solid is obtained with a melting range of 130–136° C. after drying.

$\overline{Mn}$ (by GPC): 2830 g/mol
Polydispersity $\overline{Mw}/\overline{Mn}$: 1.22

Figure 2:
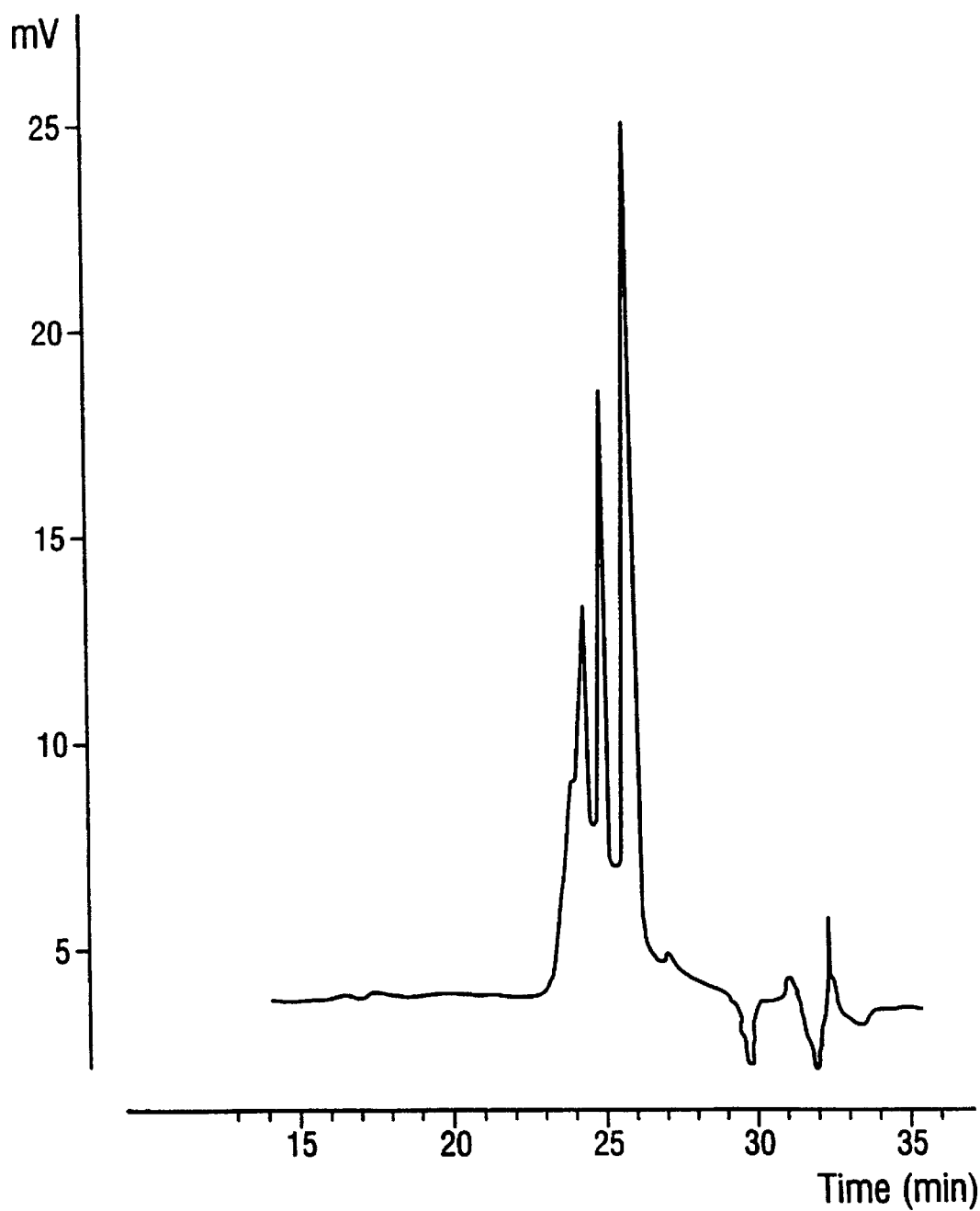

The GPC analysis shows a chromatogram as in FIG. 2.

The ratio of the three main single components ((n'=2):(n'=4):(n'=6)) of the polydispers product obtained is in molar % 2:0.96:0.33.

EXAMPLE 1

Preparation of the Product of the Formula

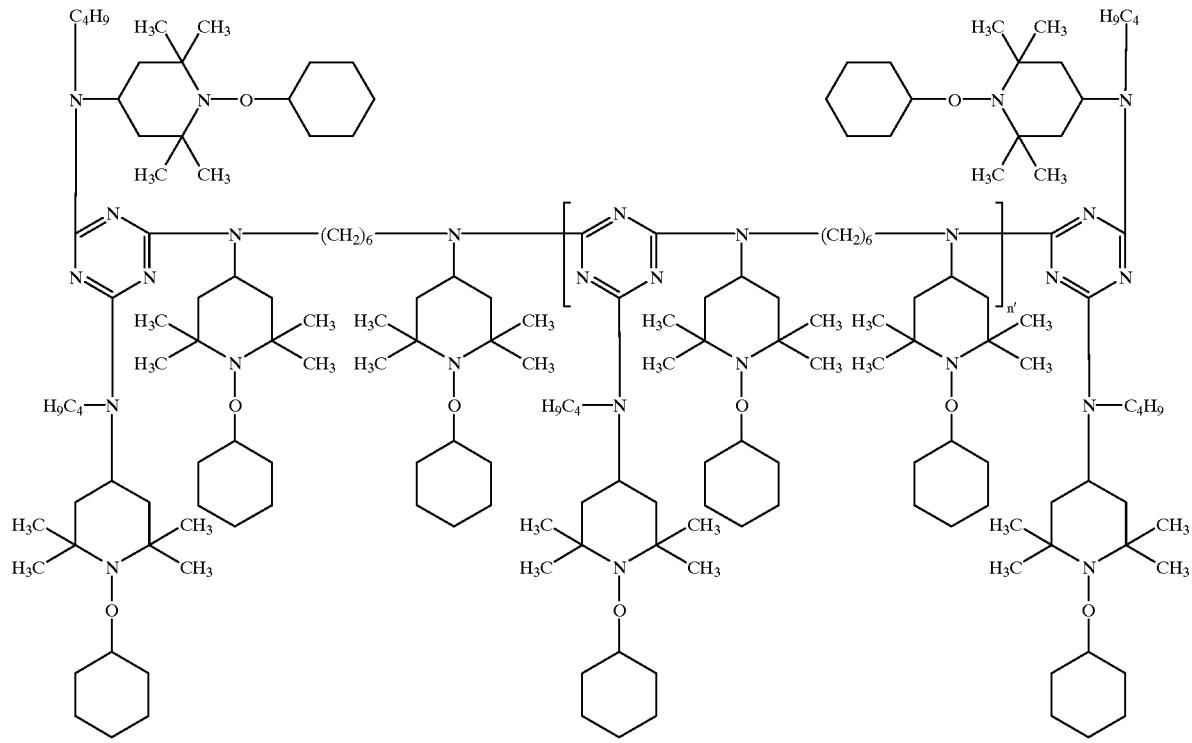

A magnetically stirred 500 ml 4 necked round bottom flask is charged with 25.0 g (0.115 moles) of the product of Example S-1 and 200 ml of cyclohexane. The mixture is heated to reflux and 0.10 9 of $MoO_3$ are added. 51.9 g (0.403 moles) of 70% t-butylhydroperoxide are added over 3 hours and water is separated by azeotropic distillation. Three additional 0.10 g portions of $MoO_3$ are added during the course of this addition. The contents are transferred to a magnetically stirred ®Fisher-Porter pressure bottle and heated at 125° C. for four hours, then cooled below 60° C. and $MoO_3$ is filtered. The filtrate is stirred in the presence of 200 ml of 5% $Na_2SO_3$ for 90 minutes. Phases are separated and the organic phase is washed with water and aqueous saturated NaCl. The organic phase is dried over $MgSO_4$ and evaporated to a pale yellow solid.

Yield: 35.7 g (99% of theory).

Melting range: 130–170° C.

$^1$H NMR: 0.85–2.40 ppm (complex mixture); 3.20–3.45 ppm (s, broad, $NCH_2$); 3.54–3.70 ppm (s, broad, NOCH); 4.90–5.50 ppm (s, broad, NCH). Ratio of protons at 3.20, 3.54 and 4.90 ppm is 2:1:1.

$^3$C NMR: 82 ppm (NOC); 165 ppm (triazine C).

EXAMPLE 2

Preparation of the Product of the Formula

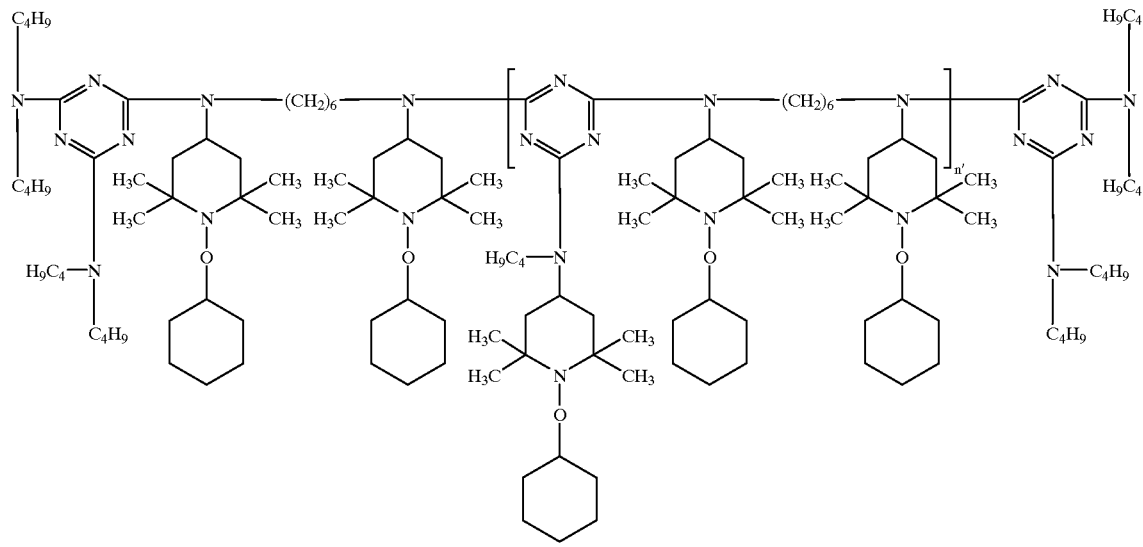

A magnetically stirred 500 ml 4 necked round bottom flask is charged with 25.0 g (0.0962 moles) of the product of Example S-2 and 200 ml of cyclohexane. The mixture is heated to reflux and 0.10 g of MoO$_3$ are added. 43.3 g (0.337 moles) of 70% t-butylhydroperoxide are added over 2 hours and water is separated by azeotropic distillation. Two additional 0.10 g portions of MoO$_3$ are added during the course of this addition. The contents along with an additional 0.3 g of MoO$_3$ are transferred to a magnetically stirred ®Fisher-Porter pressure bottle and heated at 125° C. for eleven hours, then cooled below 60° C. and MoO$_3$ is filtered. The filtrate is stirred in the presence of 200 ml of 5% Na$_2$SO$_3$ for 90 minutes. Phases are separated and the organic phase is washed with water and aqueous saturated NaCl. The organic phase is dried over MgSO$_4$ and evaporated to a pale yellow solid.

Yield: 34.4 g (99% of theory).

Melting range: 128–169° C.

$^1$H NMR: 0.80–2.50 ppm (complex mixture); 3.20–3.40 ppm (s. broad, NCH$_2$); 3.40–3.50 (s, broad, NCH$_2$ of NC$_4$H$_9$); 3.54–3.70 ppm (s, broad, NOCH); 4.90–5.40 ppm (s, broad, NCH).

Ratio of protons at 3.20, 3.54 and 4.90 ppm is 2:1:1.

$^3$C NMR: 82 ppm (NOC); 165 ppm (triazine C).

EXAMPLE 2-A

Preparation of the Product of the Formula

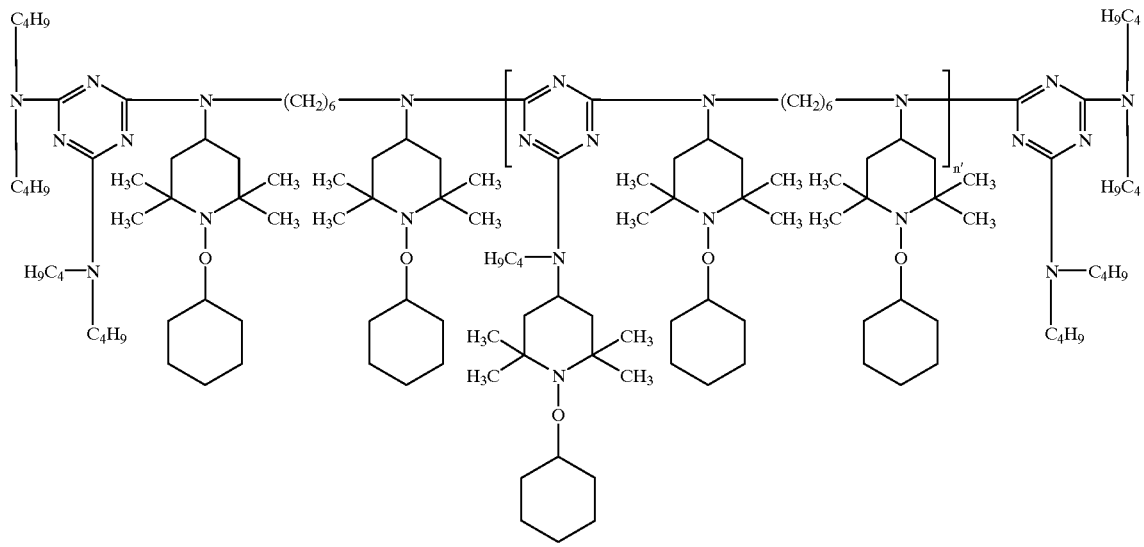

A mixture of 885 g (3.39 moles) of the product of Example S-2, 6000 g (71.4 moles) of cyclohexane and 2.2 g of molybdenum trioxide is heated to reflux. A solution of 3360 g of 70% aqueous t-butyl hydroperoxide (26.1 moles) is added to the refluxing mixture over 1–2 hours and water is removed by azeotropic distillation. The reaction mass is transferred to a pressure reactor and heated at 125° C. at 30–50 psig (2.1–3.5 bar) until the red color is discharged. The crude reaction mass is cooled and treated with aqueous sodium sulfite to destroy residual peroxide. The aqueous layer is split off and the organic layer is concentrated under reduced pressure to a melt which is fed slowly into cold methanol to obtain, after filtration, an off white solid product.

Average transmission values (10% toluene): 425 nm=44.2%; 450 nm =56.0%;

475 nm=67.5%

EXAMPLE 2-B

Preparation of the Product of the Formula

The procedure of Example 2-A is repeated, except that during work-up, the melt obtained after cyclohexane is removed is diluted with t-butyl alcohol and concentrated to 50% solids. The solution is cooled and cold methanol is rapidly added to afford, after filtration, an off white solid product.

Average transmission values (10% toluene): 425 nm=46.5%; 450 nm=63.3 0%;

475 nm=74.0%

EXAMPLE 3-A

Preparation of the Product of the Formula (Method 1)

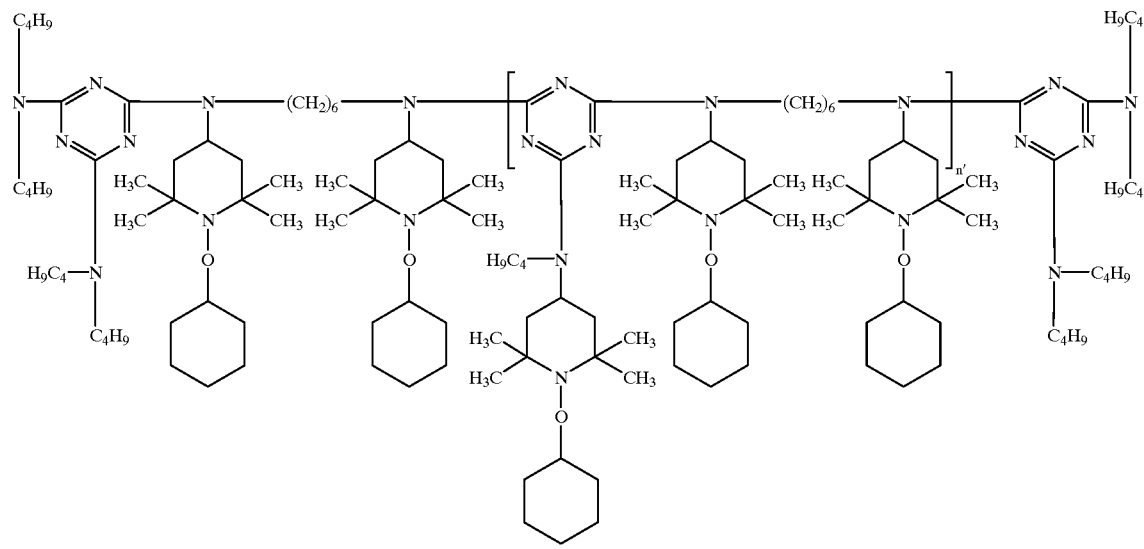

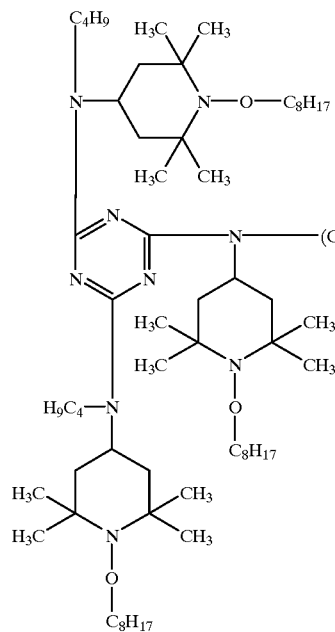
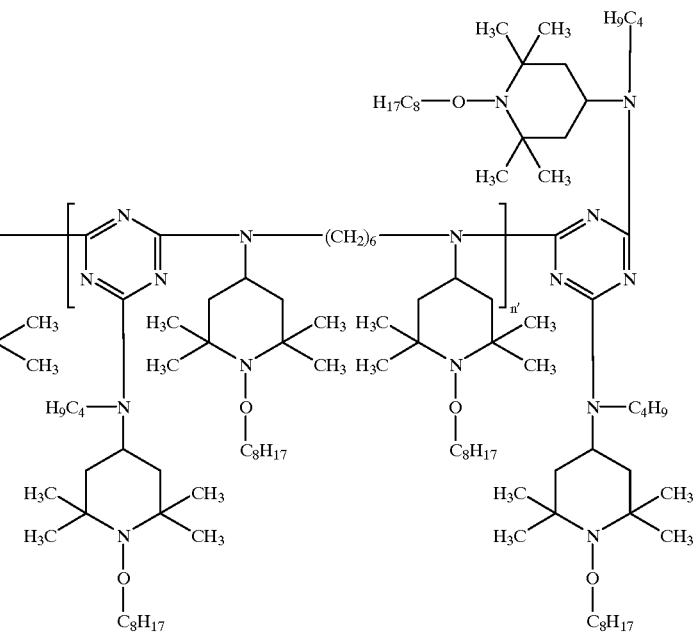

A 500 ml 4 neck round bottom flask is charged with 30.0 g (0.138 moles) of the product of Example S-1, 240 ml of n-octane, 36 g (0.27 moles) of 70% t-butylhydroperoxide and 0.2 g of $MoO_3$. The reaction mixture is heated to reflux and water is removed by azeotropic distillation. After 15 minutes an additional amount of 35.1 g (0.27 moles) of t-butylhydroperoxide and 0.1 g of $MoO_3$ are added and refluxing is continued until the reaction temperature rises to 110° C. At that point the reaction mixture is transferred to a magnetically stirred ®Fisher-Porter pressure bottle and heated at 150° C. for 3.5 hours. The catalyst is filtered off and the filtrate is slurried with 200 ml of 5% $Na_2SO_3$ for two hours. The organic phase is washed with water and aqueous saturated NaCl, dried over $MgSO_4$ and evaporated to a pale yellow solid.

Yield: 43.3 g (91% of theory).

Melting range: 93–117° C.

$^1$H NMR: 0.70–2.50 ppm (complex mixture); 3.20–3.45 ppm (s, broad, $NCH_2$); 3.55–3.95 ppm (broad, NOCH, mixture of isomers in $C_8H_{17}$); 4.90–5.50 ppm (s, broad, NCH). Ratio of protons at 3.20, 3.55 and 4.90 ppm is 2:1:1.

$^{13}$C NMR: 78–84 ppm (NOC, mixtures of isomers in $C_8H_{17}$); 165 ppm (triazine C).

EXAMPLE 3-B

Preparation of the Product of the Formula (Method 2)

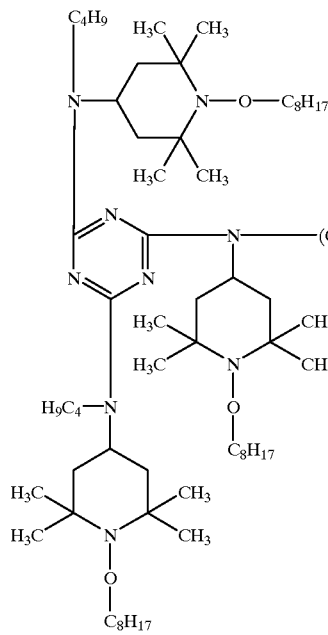
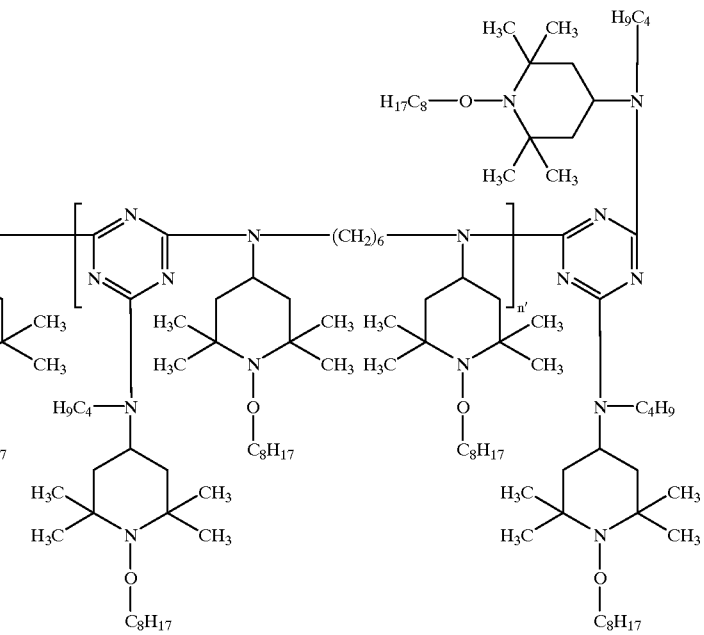

A 500 ml 4 necked round bottom flask is charged with 25.0 g (0.115 moles) of the product of Example S-1, 200 ml of n-octane and 0.3 g of $MoO_3$. The mixture is heated to reflux and 59.2 g (0.46 moles) of 70% t-butylhydroperoxide is added over a period of 45 minutes with continuous separation of water by azeotropic distillation. After 5 hours additional 22.2 g (0.17 moles) of t-butylhydroperoxide and 0.2 g of $MoO_3$ are added. After a total reaction time of 9 hours the catalyst is filtered off and the filtrate is slurried with 200 ml of 5% $Na_2SO_3$ for two hours. The organic phase is washed with water and aqueous saturated NaCl, dried over $MgSO_4$ and evaporated to a pale yellow solid.

Yield: 37.3 9 (99% of theory).

Melting range: 108–124° C. $^1$H- and $^{13}$C-NMR: The NMR are identical to the product prepared according to Method 1 as described in Example 3-A.

EXAMPLE 4

Preparation of the Product of the Formula minutes an additional amount of 29.4 g (0.23 moles) of t-butylhydroperoxide and 0.2 g of $MoO_3$ are added and refluxing is continued until the reaction temperature rises to 110° C. At that point the reaction mixture is transferred to a magnetically stirred ®Fisher-Porter pressure bottle and heated at 150° C. for 3.5 hours. The catalyst is filtered off and the filtrate is slurried with 200 ml of 5% $Na_2SO_3$ for two hours. The organic phase is washed with water and aqueous saturated NaCl, dried over $MgSO_4$ and evaporated to a pale yellow solid.

Yield: 41.0 g (92% of theory).

Melting range: 95–125° C.

$^1$H NMR: 0.80–2.50 ppm (complex mixture); 3.20–3.41 ppm (s, broad, $NCH_2$); 3.41–3.55 (s, broad, $NCH_2$ of $NC_4H_9$); 3.55–3.95 ppm (broad, NOCH, mixture of isomers in $C_8H_{17}$); 4.90–5.50 ppm (s, broad, NCH). Ratio of protons at 3.20, 3.55 and 4.90 ppm is 2:1:1.

$^{13}$C NMR: 76–84 ppm (NOC, mixtures of isomers in $C_8H_{17}$); 165 ppm (triazine C).

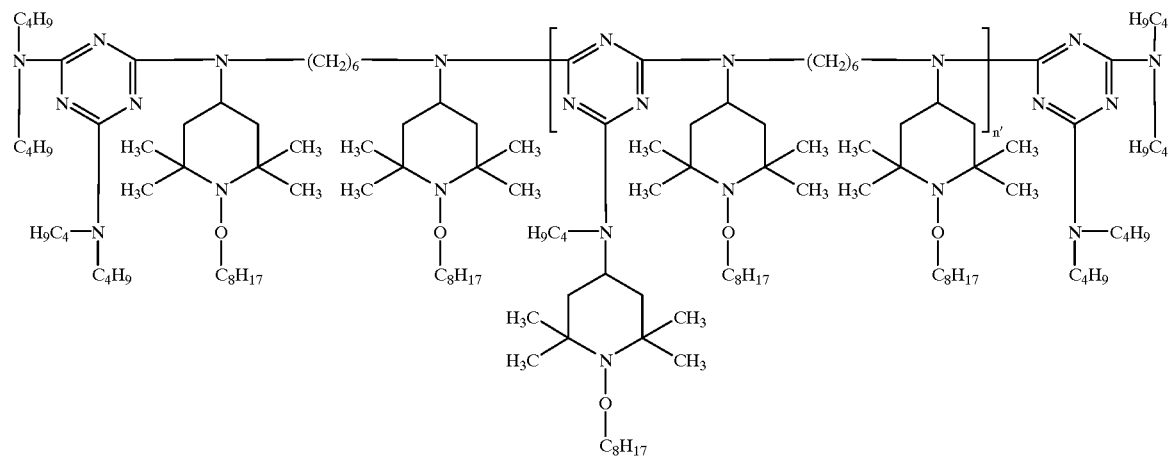

A 500 ml 4 neck round bottom flask is charged with 30.0 9 (0.115 moles) of the product of Example S-2, 240 ml of n-octane, 30 g (0.23 moles) of 70% t-butylhydroperoxide and 0.2 g of $MoO_3$. The ireaction mixture is heated to reflux and water is removed by azeotropic distillation. After 30

EXAMPLE 4-A

Preparation of the Product of the Formula

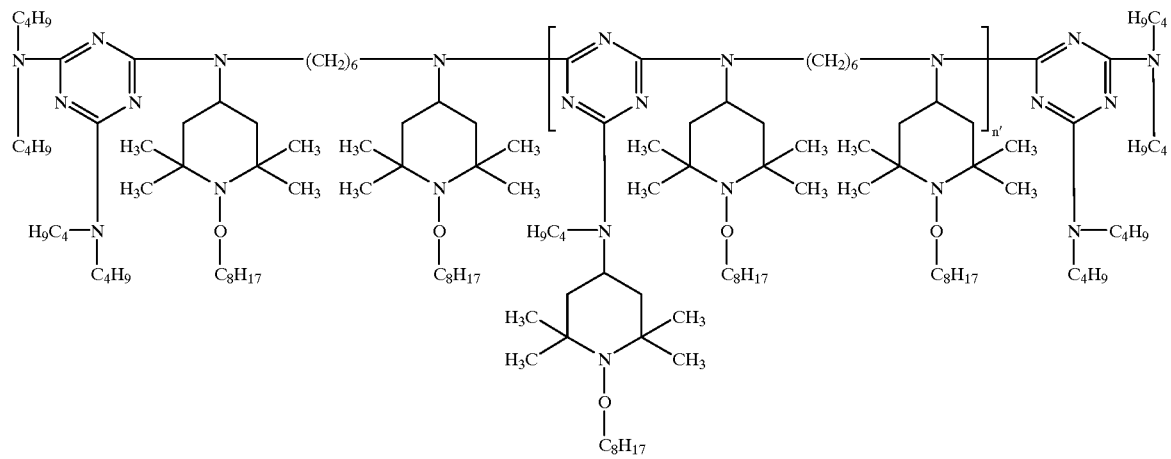

A mixture of 1304 g (5.0 moles) of the product of Example S-2, 10.3 kg (90.2 moles) of octane and 8.95 g of molybdenum trioxide is heated to reflux. A solution of 3873 g of 70% aqueous t-butyl hydroperoxide (30.1 moles) is added to the refluxing mixture over 1–2 hours and water is removed by azeotropic distillation. The reaction mass is heated at reflux at atmospheric pressure until the red color is discharged. The crude reaction mass is cooled and treated with aqueous sodium sulfite to destroy residual peroxide. The aqueous layer is split off and the organic layer is concentrated under reduced pressure to a melt which is fed slowly into cold methanol to obtain, after filtration, an off white solid product.

Average transmission values (10% toluene): 425 nm=47.7%; 450 nm=76.0%;
475 nm=84.6

EXAMPLE 4-B

Preparation of the Product of the Formula

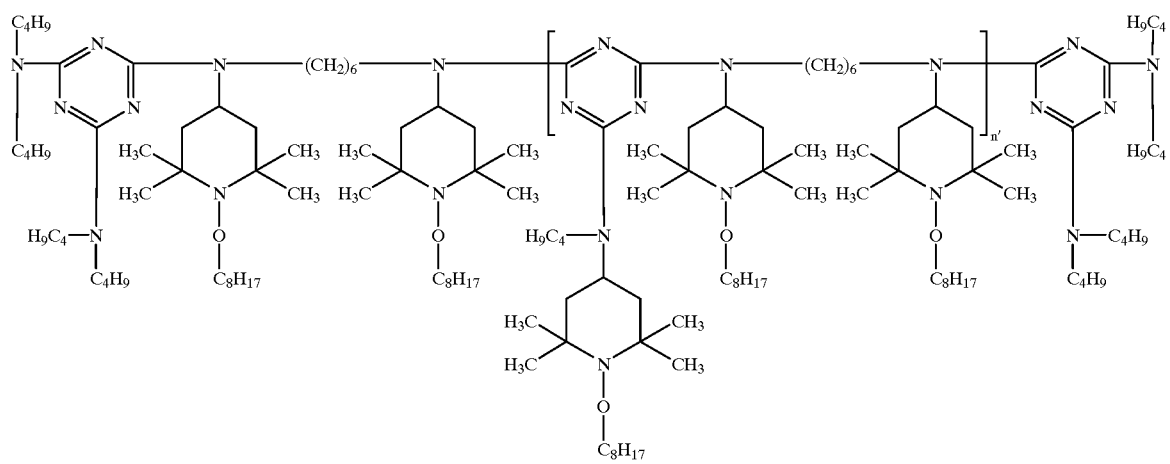

The procedure of Example 4-A is repeated, except that during work-up, the melt obtained after octane is removed is diluted with t-butyl alcohol and concentrated to 50% solids. The solution is cooled and cold methanol is rapidly added to afford, after filtration, an off white solid product.

Average transmission values (10% toluene): 425 nm=47.6%; 450 nm=80.0%;
475 nm=91.4%

EXAMPLE A

Pigmented thermoplastic olefin (TPO) pellets are prepared by mixing a polyolefin blend (polypropylene containing an ethylene-propylene copolymer; ®Polytrope TPP 518-01 from ®A. Schulman, Inc.; Akron, Ohio, USA) with the additives listed below in a ®Superior/MPM 1" single screw extruder with a general all-purpose screw (24:1 L/D) at 200° C., cooling in a water bath and pelletizing. Prior to extrusion and molding, the additives are dry blended in a tumble dryer.

Additives 0.25%*) of ®Red 3B (Pigment Red 177, Color Index 65300), 0.2%*) of 2-(2'-hydroxy-3',5'-di-tert-amylphenyl)benztriazol, 0.2%*) of bis(11-octyloxy-2,2,6,6-tetramethyl-4-piperidyl)sebacate, 0.1%) of calcium stearate, about 10%*) of talc and the stabilizers listed in Table 1

*) weight percent based on the polyolefin blend

The resulting pellets are molded into 1.524 mm thick 2"×2" plaques at about 190° C. on a ®BOY 30M Injection Molding Machine.

The test plaques are mounted in metal frames and exposed in an ®Atlas Ci65 Xenon Arc Weather-O-Meter at 70° C. black panel temperature, 0.55 W/m$^2$ at 340 nanometers and 50% relative humidity with intermittent light/dark cycles and water spray (®Society of Automotive Engineers—SAE J 1960 Test Procedure—Exterior Automotive conditions).

Gloss measurements of the test specimens are conducted on a ®BYK-GARDNER Haze/Gloss Meter at 60° according to ASTM D 523.

The results are shown in Table 1.

TABLE 1

| | Gloss Retention after hours Weather-O-Meter | |
|---|---|---|
| Stabilizers | 0 hours (≈ 0 kJ/m$^{2**}$) | 1890 hours (≈ 2500 kJ/m$^{2**}$) |
| 0.05%*) of pentaerythritol tetrakis [3-(3,5-di-tert-butyl-4-hydroxyphenyl) propionate], 0.05%*) of tris[2,4-di-tert-butylphenyl] phosphite, 0.20%*) of the compound of Example 2 | 100.0% | 87.1% |
| 0.05%*) of pentaerythritol tetrakis [3-(3,5-di-tert-butyl-4-hydroxyphenyl) propionate], 0.05%*) of tris[2,4-di-tert-butylphenyl] phosphite, 0.20%*) of the compound of Example 4 | 100.0% | 89.3% |
| 0.05%*) of di(hydrogenated tallow) hydroxylamine 0.20%*) of the compound of Example 2 | 100.0% | 88.3% |

TABLE 1-continued

| | Gloss Retention after hours Weather-O-Meter | |
|---|---|---|
| Stabilizers | 0 hours (≙ 0 kJ/m²**) | 1890 hours (≙ 2500 kJ/m²**) |
| 0.05%*) of di(hydrogenated tallow) hydroxylamine 0.20%*) of the compound of Example 4 | 100.0% | 83.4% |

*) weight percent based on the polyolefin blend
**) refers to incident energy expressed as kJ/m² measured at 340 nm The formulations containing the stabilizers listed in Table 1 show much greater resistance to photodegradation than those without said stabilizers. The unstabilized test specimens fail quickly under the UV exposure outlined above.

EXAMPLE B

Stabilization of Polypropylene Tapes 1.0 g of the compound of Example 2 or 4, 0.5 g of pentaerythritol tetrakis[3-(3,5-di-tert-butyl-4-hydroxyphenyl)propionate] and 1 g of calcium stearate are mixed in a turbomixer with 1000 g of polypropylene powder (PP ®MOPLEN S 30 S) having a melt index of 2.1 (measured at 230° C. and 2.16 kg).

The mixtures are extruded at 200–230° C. to granules; these granules are subsequently converted to stretched tapes of 50 μm thickness and 2.5 mm width using a pilot plant (®Leonard; Sumirago/VA, Italy) under the following conditions:

| Extruder temperature | 210–230° C. |
|---|---|
| Head temperature | 240–260° C. |
| Stretch ratio | 1:6 |

The tapes thus pretreated are mounted on a white card and exposed in a Weather-O-Meter 65 WR (ASTM D 2565-85) with a black panel temperature of 63° C.

The residual tenacity is measured, by means of a constant velocity tensometer, on a sample taken after various light exposure times; from this, the exposure time (in hours) required to halve the initial tenacity ($T_{50}$) is measured.

The results reveal that the compound of Example 2 or 4 stabilizes polypropylene tapes in excellent manner.

EXAMPLE C

Stabilization of Polyethylene Films—Treated and Untreated with Pesticides

The compound of Example 2 or 4 is mixed via masterbatch with low density polyethylene (LDPE) pellets (Riblene® FF 29 supplied by ®ENICHEM, Milano, Italy; density: 0.921 g/cm³; melt flow index at 190° C. and 2.16 kg: 0.60 g/10 min) in a slow mixer.

The masterbatch is previously prepared by extruding powdered LDPE and 5% by weight of the compound of Example 2 or 4 with a double screw extruder at 200° C.

The mixture is blown at 200° C. Films of thickness 150 μm are obtained, containing 0.2% of the compound of Example 2 or 4.

Some of the films are treated with pesticides as follows: The films are stored before Weather-O-Meter exposure for 20 days over a concentrated solution of VAPAM® in water (1:1 ratio in parts by volume) without direct contact with the solution. (VAPAM® (®BASLINI SpA, Treviglio/BG, Italy) is an aqueous solution of 382 g per liter of metam-sodium having the formula $CH_3$—NH—CS—SNa.)

After the above treatment, film samples are exposed on a white cardboard in a Weather-O-Meter Type 65WR with a black panel temperature of 63° C. Untreated films are exposed as well under the same conditions. The degradation process is monitored by measuring the increase of carbonyl in the sample with a Fourier Transform Infrared Spectrophotometer. A high increase of carbonyl indicates high degradation. Degradation is also monitored by measuring the residual elongation, by means of a constant velocity tensometer, on a sample taken after various exposure times. The exposure time, in hours, required to halve the initial elongation ($T_{50}$) is calculated.

The results reveal that the compound of Example 2 or 4 stabilizes polyethylene films in excellent manner.

EXAMPLE D

Greenhouse Application

The compound of Example 2 or 4 is mixed via masterbatch with polyethylene of low density (LDPE) pellets (Riblene® EF 2100 V supplied by ®ENICHEM, Milano, Italy; density: 0.921 g/cm³; melt flow index at 190° C. and 2.16 kg: 0.25) in a slow mixer.

The masterbatch is previously prepared by extruding powdered LDPE and 10% by weight of the compound of Example 2 or 4.

The mixture is blow extruded at 200° C., and films of 150 microns thickness are obtained, containing 0.3% or 0.4% of the compound of Example 2 or 4.

The films are exposed on the south-facing roof of a greenhouse in Pontecchio Marconi (Bologna, Italy) without backing, on galvanized iron backing and on pine wood backing.

The following pesticides are applied in the greenhouse: VAPAM® (®BASLINI SpA, Treviglio/BG, Italy) which is an aqueous solution of 382 g per liter of metam-sodium having the formula $CH_3$—NH—CS—SNa. SESMETRIN® (®BIMEX SpA, Isola/VI, Italy) which is a 23.75% (% w/w) aqueous solution of permethrin having the formula

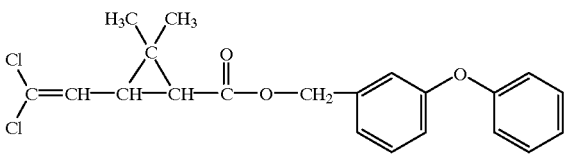

The greenhouse is treated with a solution of 4 liters of ®VAPAM in 10 liters of water every 6 months, and with ®SESMETRIN (5 g in 5 liters of water) every month.

During the exposure, the performance is periodically evaluated measuring the residual elongation (in % of the initial elongation of the polyethylene film) by means of a dynamometer at constant speed.

The results reveal that the compound of Example 2 or 4 stabilizes the LDPE film in excellent manner.

EXAMPLE E

Stabilization of Low Density Polyethylene Films— Outdoor Exposure

The compound of Example 2 or 4 is mixed via masterbatch with polyethylene of low density (LDPE) pellets (Riblene® EF 2100 V supplied by ®ENICHEM, Milano, Italy; density: 0.921 g cm³; melt flow index at 190° C. and 2.16 kg: 0.25) in a slow mixer.

The masterbatch is previously prepared by extruding powdered LDPE and 10% by weight of the compound of Example 2 or 4.

The mixture is blow extruded at 200° C., and films of 150 microns thickness are obtained, containing 0.3% or 0.4% of the compound of Example 2 or 4.

The films are exposed in Pontecchio Marconi (about 110 kLys/year irradiation) without support, on galvanized iron and on pine wood support, without application of pesticides. The films surfaces are fixed in a 45° inclination towards south.

During the exposure, the performance is periodically evaluated measuring the residual elongation (in % of the initial elongation of the polyethylene film) by means of a dynamometer at constant speed.

The results reveal that the compound of Example 2 or 4 stabilizes the LDPE film in excellent manner.

EXAMPLE F

Fiber grade polypropylene containing 0.05% by weight of calcium stearate and 0.05% by weight of di(hydrogenated tallow) hydroxylamine as base stabilization is dry blended with the stabilizer indicated in Table 2 and then melt compounded at 234° C. into pellets. The pelletized fully formulated resin is then spun at 246° C. or 274° C. into fiber using a ®Hills laboratory model fiber extruder. The spun tow of 41 filaments is stretched at a ratio of 1:3.2 to give a final denier of 615/41.

"Socks" are knitted from the stabilized polypropylene on a ®Lawson-Hemphill Analysis Knitter and exposed in an ®Atlas Xenon-Arc-Weather-Ometer using SAE J1885 Interior Automotive conditions at 89° C. bpt, 0.55 kW/cm² at 340 nm with no spray cycle. Failure in this test is determined by the observation of the physical failure of the sock when it is "scratched" with a blunt glass rod. The longer it takes for this catastrophic failure to occur, the more effective is the stabilizer. The results are shown in Table 2.

TABLE 2

| Stabilizer | Catastrophic Failure Time Fiber Spun at 246° C. | Catastrophic Failure Time Fiber Spun at 274° C. |
|---|---|---|
| None | 192 hours | 96 hours |
| 0.25% by weight of the compound of Example 2 | 408 hours | 408 hours |
| 0.25% by weight of the compound of Example 4 | 600 hours | 408 hours |

What is claimed is:

1. A product obtained by transforming groups of the formula (G-I)

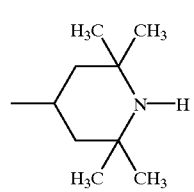

(G-I)

being present in a block oligomer having a polydispersity $\overline{M}w/\overline{M}n$ of 1 to 1.7 and corresponding to the formula (I)

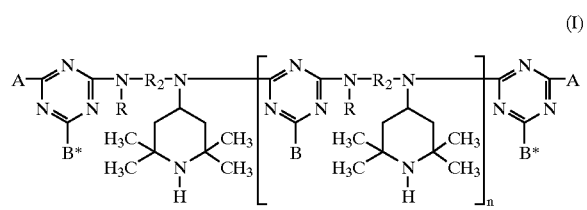

(I)

to groups of the formula (G-II);

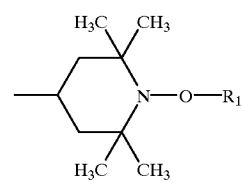

(G-II)

wherein $R_1$ is a hydrocarbyl radical or —O—$R_1$ is oxyl; said transformation is carried out by reaction of the block oligomer corresponding to the formula (I) with a hydroperoxide in a hydrocarbon solvent in the presence of a peroxide decomposing catalyst;

n is a number from 2 to 14;

the radicals $R_2$ are independently of one another $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi-($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below; or $R_2$ is a group of the formula (a), (b) or (c);

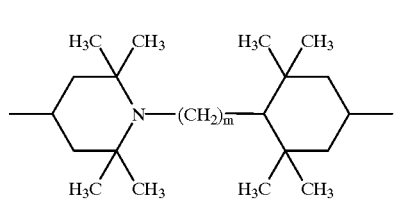

(a)

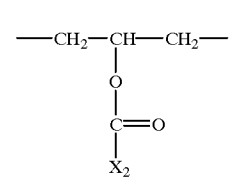

(b)

-continued

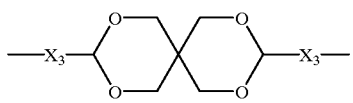
(c)

with m being 2 or 3, $X_2$ being $C_{12}$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

the radicals A are independently of one another —$OR_3$, —$N(R_4)(R_5)$ or a group of the formula (11);

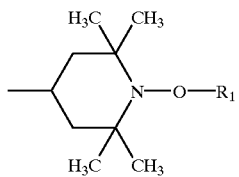
(G-II)

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

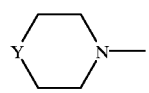
(III)

with Y being —O—, —$CH_2$—, —$CH_2CH_2$— or >N—$CH_3$;

and $R_3$ is additionally hydrogen or —$N(R_4)(R_5)$ is additionally a group of the formula (III);

X is —O— or >N—$R_6$;

$R_6$ is $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (G-I), or $C_2$–$C_4$alkyl which is substituted in the 2, 3 or 4 position by —OH, $C_1$–$C_8$alkoxy, di($C_1$–$C_4$alkyl)amino or a group of the formula (III);

the radicals R have independently of one another one of the meanings given for $R_6$; and the radicals B and B* have independently of one another one of the meanings given for A;

with the proviso that in the individual recurrent units of the formula (I), each of the radicals B, R and $R_2$ has the same or a different meaning.

2. A product according to claim 1, wherein $R_1$ is $C_5$–$C_{18}$alkyl, $C_5$–$C_{18}$alkenyl, $C_5$–$C_{18}$alkynyl, $C_5$–$C_{12}$cycloalkyl unsubstituted or substituted by $C_1$–$C_4$alkyl; $C_5$–$C_{12}$cycloalkenyl unsubstituted or substituted by $C_1$–$C_4$alkyl; a bicyclic or tricyclic hydrocarbyl having 6 to 10 carbon atoms or $C_7$–$C_9$phenylalkyl unsubstituted or substituted on the phenyl by $C_1$–$C_4$alkyl; and the hydrocarbon solvent is, dependent on $R_1$, $C_5$–$C_{18}$alkane, $C_5$–$C_{18}$alkene, $C_5$–$C_{18}$alkyne, $C_5$–$C_{12}$cycloalkane unsubstituted or substituted by $C_1$–$C_4$alkyl; $C_5$–$C_{12}$cycloalkene unsubstituted or substituted by $C_1$–$C_4$alkyl; a bicyclic or tricyclic hydrocarbon having 6 to 10 carbon atoms or $C_7$–$C_9$phenylalkane unsubstituted or substituted on the phenyl by $C_1$–$C_4$alkyl.

3. A product according to claim 1, wherein $R_1$ is heptyl, octyl, cyclohexyl, methylcyclohexyl, cyclooctyl, cyclohexenyl, α-methylbenzyl or 1,2,3,4-tetrahydronaphthenyl, and the hydrocarbon solvent is, dependent on $R_1$, heptane, octane, cyclohexane, methylcyclohexane, cyclooctane, cyclohexene, ethylbenzene or tetralin.

4. A product according to claim 1, wherein $R_1$ is cyclohexyl or octyl, and the hydrocarbon solvent is, dependent on $R_1$, cyclohexane or octane.

5. A product according to claim 1, wherein the radical —O—$R_1$ is oxyl and the hydrocarbon solvent is an inert organic solvent.

6. A product according to claim 1, wherein the peroxide decomposing catalyst is a metal carbonyl, metal oxide, metal acetylacetonate or a metal alkoxide where the metal is selected from the groups IVb, Vb, VIb, VIIb and VIII of the periodic table.

7. A product according to claim 1, wherein the hydroperoxide is t-butyl hydroperoxide and the peroxide decomposing catalyst is $MoO_3$.

8. A product according to claim 1, wherein per mole of the group of the formula (G-I)

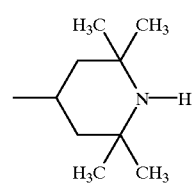
(G-I)

being present in the block oligomer corresponding to the formula (I) 2 to 8 moles of the hydroperoxide, 0.001 to 0.1 mole of the peroxide decomposing catalyst and 5 to 30 moles of the hydrocarbon solvent are applied.

9. A product according to claim 1, wherein the polydispersity $\overline{Mw}/\overline{Mn}$ of the block oligomer corresponding to the formula (I) is 1.1 to 1.7.

10. A product according to claim 1, wherein R is a group of the formula (G-I).

11. A product according to claim 1 wherein $R_2$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by —O— or >N—X$_1$ with X$_1$ being C$_1$–C$_{12}$acyl or (C$_1$–C$_{12}$alkoxy)carbonyl or having one of the definitions of R$_4$; or R$_2$ is a group of the formula (b);

R$_3$, R$_4$ and R$_5$, which are identical or different, are C$_1$–C$_{18}$alkyl, C$_5$–C$_{12}$cycloalkyl which is unsubstituted or substituted by 1, 2 or 3 C$_1$–C$_4$alkyl; phenyl which is unsubstituted or substituted by 1, 2 or 3 C$_1$–C$_4$alkyl or C$_1$–C$_4$alkoxy; C$_7$–C$_9$phenylalkyl which is unsubstituted or substituted on the phenyl by 1, 2 or 3 C$_1$–C$_4$alkyl;

and R$_3$ is additionally hydrogen or —N(R$_4$)(R$_5$) is additionally a group of the formula (III);

R$_6$ is C$_1$–C$_{18}$alkyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; or a group of the formula (G-I).

12. A product according to claim 1, wherein n is a number from 2 to 12;

R$_2$ is C$_2$–C$_{12}$alkylene, C$_5$–C$_7$cycloalkylene, C$_5$–C$_7$cycloalkylenedi(C$_1$–C$_4$alkylene), C$_1$–C$_4$alkylenedi(C$_5$–C$_7$cycloalkylene) or phenylenedi(C$_1$–C$_4$alkylene);

R$_6$ is C$_1$–C$_{18}$alkyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; or a group of the formula (G-I); and R is a group of the formula (G-I).

13. A product according to claim 1, wherein

R$_2$ is C$_2$–C$_{10}$alkylene, cyclohexylene, cyclohexylenedi(C$_1$–C$_4$alkylene), C$_1$–C$_4$alkylenedicyclohexylene or phenylenedi(C$_1$–C$_4$alkylene);

R$_3$, R$_4$ and R$_5$, which are identical or different, are C$_1$–C$_{12}$alkyl, C$_5$–C$_7$cycloalkyl which is unsubstituted or substituted by 1, 2 or 3 C$_1$–C$_4$alkyl; phenyl which is unsubstituted or substituted by 1, 2 or 3 C$_1$–C$_4$alkyl; or benzyl which is unsubstituted or substituted on the phenyl by C$_1$–C$_4$alkyl; or —N(R$_4$)(R$_5$) is additionally a group of the formula (III); and R$_6$ is C$_1$–C$_{12}$alkyl, C$_5$–C$_7$cycloalkyl which is unsubstituted or substituted by 1, 2 or 3 C$_1$–C$_4$alkyl; benzyl which is unsubstituted or substituted on the phenyl by 1, 2 or 3 C$_1$–C$_4$alkyl; or a group of the formula (G-I).

14. A product according to claim 1, wherein

R$_2$ is C$_2$–C$_8$alkylene;

R$_3$, R$_4$ and R$_5$, which are identical or different, are C$_1$–C$_8$alkyl, cyclohexyl which is unsubstituted or substituted by methyl; phenyl which is unsubstituted or substituted by methyl; or benzyl; or —N(R$_4$)(R$_5$) is additionally 4-morpholinyl; and R$_6$ is C$_1$–C$_8$alkyl, cyclohexyl which is unsubstituted or substituted by methyl; benzyl or a group of the formula (G-I).

15. A product according to claim 1, wherein n is a number from 2 to 6;

R$_2$ is C$_2$–C$_6$alkylene;

A is —N(R$_4$)(R$_5$) or a group of the formula (II);

R$_4$ and R$_5$, which are identical or different, are C$_1$–C$_8$alkyl;

or —N(R$_4$)(R$_5$) is additionally 4-morpholinyl;

X is >NR$_6$;

R$_6$ is C$_1$–C$_4$alkyl; and the radicals B and B* have independently of one another one of the definitions given for A.

16. A product according to claim 1, wherein B* is different from B and each of the radicals B, R and R$_2$ has the same meaning in the individual recurring units of the formula (I).

17. A product obtained by hydrogenating a product according to claim 1, wherein —OR$_1$ in the formula (G-II) is oxyl to obtain a block oligomer with groups of the formula (G-III):

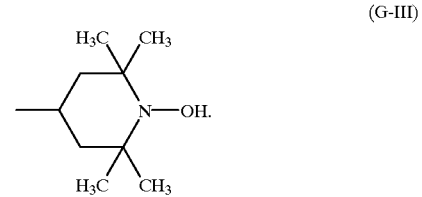

(G-III)

18. A mixture containing a) a monodispers compound of the formula (Ia),

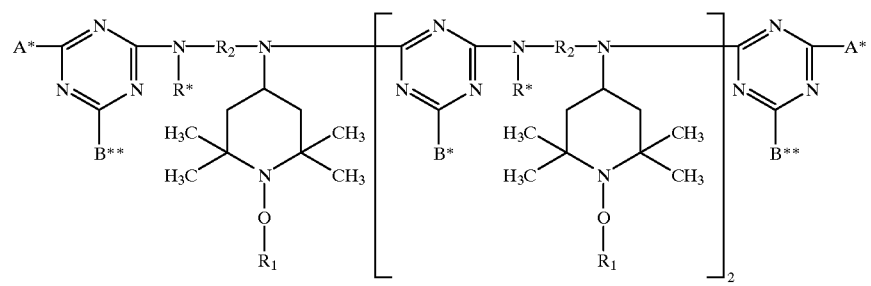

(Ia)

b) a monodispers compound of the formula (Ib) and

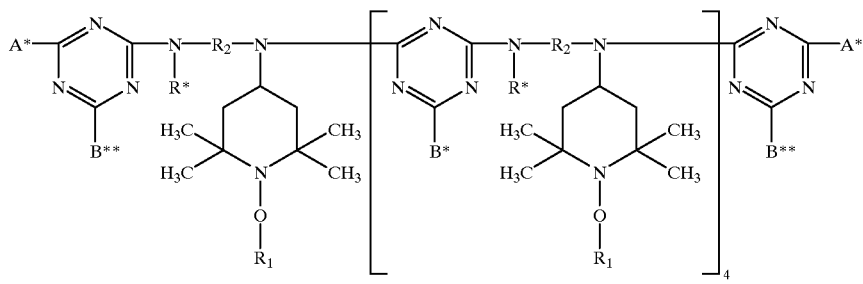
(Ib)

c) a monodispers compound of the formula (Ic)

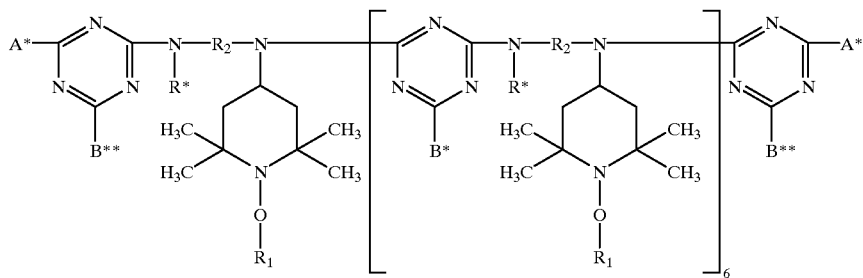
(Ic)

the compounds of the formulae (Ia), (Ib) and (Ic) differ only in the number of the repetitive units, the ratio of the compounds of the formula (Ia) to (Ib) to (Ic) in molar % is 2:1.6:1 to 2:0.4:0.04; and $R_1$ is hydrogen, a hydrocarbyl radical or —O—R, is oxyl;

$R_2$ is $C_2$–$C_{12}$alkylene, $C_4$–$C_{12}$alkenylene, $C_5$–$C_7$cycloalkylene, $C_5$–$C_7$cycloalkylenedi($C_1$–$C_4$alkylene), $C_1$–$C_4$alkylenedi-($C_5$–$C_7$cycloalkylene), phenylenedi($C_1$–$C_4$alkylene) or $C_4$–$C_{12}$alkylene interrupted by 1,4-piperazinediyl, —O— or >N—$X_1$ with $X_1$ being $C_1$–$C_{12}$acyl or ($C_1$–$C_{12}$alkoxy)carbonyl or having one of the definitions of $R_4$ given below; or $R_2$ is a group of the formula (a), (b) or (c);

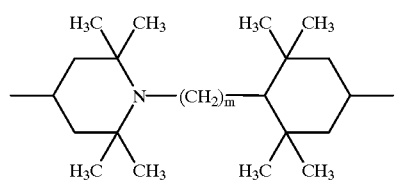
(a)

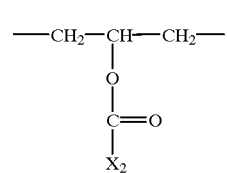
(b)

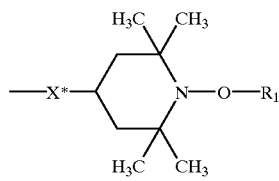
(c)

with m being 2 or 3, $X_2$ being $C_1$–$C_{18}$alkyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; and the radicals $X_3$ being independently of one another $C_2$–$C_{12}$alkylene;

$A^*$ is —$OR_3$, —$N(R_4)(R_5)$ or a group of the formula (G-IV);

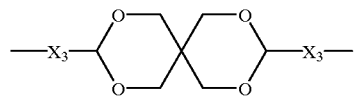
(G-IV)

$R_3$, $R_4$ and $R_5$, which are identical or different, are $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl)amino or a group of the formula (III);

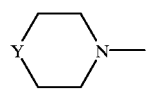

(III)

with Y being —O—, —CH$_2$—, —CH$_2$CH$_2$— or >N—CH$_3$;
and R$_3$ is additionally hydrogen or —N(R$_4$)(R$_5$) is additionally a group of the formula (III);
X* is —O— or >N—R$_6$*;
R$_6$* is C$_1$–C$_{18}$alkyl, C$_3$–C$_{18}$alkenyl, C$_5$–C$_{12}$cycloalkyl which is unsubstituted or substituted by 1, 2 or 3 C$_1$–C$_4$alkyl; C$_7$–C$_9$phenylalkyl which is unsubstituted or substituted on the phenyl by 1, 2 or 3 C$_1$–C$_4$alkyl; tetrahydrofurfuryl, a group of the formula (G-II),

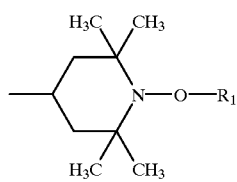

(G-II)

or C$_2$–C$_4$alkyl which is substituted in the 2, 3 or 4 position by —OH, C$_1$–C$_8$alkoxy, di(C$_1$–C$_4$alkyl)amino or a group of the formula (III);
R* has one of the meanings given for R$_6$*; and
the radicals B* and B** have independently of one another one of the meanings given for A*.

19. A mixture according to claim 18, wherein the ratio of the compounds of the formula (Ia) to (Ib) to (Ic) in molar % is 2:1.2:0.5 to 2:0.4:0.04.

20. A mixture according to claim 18, wherein the ratio of the compounds of the formula (Ia) to (Ib) to (Ic) in molar % is 2:1:0.4 to 2:0.45:0.04.

21. A mixture according to claim 18, wherein
R$_1$ is cyclohexyl or octyl;
R$_2$ is C$_2$–C$_6$alkylene;
A* and B** which are identical or different are —N(C$_1$–C$_8$alkyl)$_2$ or a group of the formula (G-IV-1)

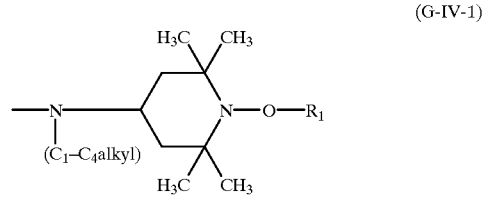

(G-IV-1)

B* is a group of the formula (G-IV-1); and
R* is a group of the formula (G-II).

22. A composition containing an organic material susceptible to degradation induced by light, heat or oxidation and a product according to claim 1.

23. A composition according to claim 22, wherein the organic material is a synthetic polymer.

24. A composition according to claim 22, wherein the organic material is polyethylene or polypropylene.

25. A composition containing an organic material susceptible to degradation induced by light, heat or oxidation and a mixture according to claim 18.

26. A method for stabilizing an organic material against degradation induced by light, heat or oxidation, which comprises incorporating into said organic material a product according to claim 1.

* * * * *